United States Patent
Ottonello et al.

(10) Patent No.: US 9,533,927 B2
(45) Date of Patent: Jan. 3, 2017

(54) CONVERSION OF A LOW VISCOSITY LIGNO-CELLULOSIC BIOMASS SLURRY INTO POLYOLS

(71) Applicant: Biochemtex S.p.A., Tortona (IT)

(72) Inventors: Piero Ottonello, Milan (IT); Paolo Torre, Arenzano (IT); Dario Giordano, Tortona (IT); Stefano Paravisi, Tortona (IT); Chiara Prefumo, Genoa (IT); Pietro Pastorino, Campo Ligure (IT)

(73) Assignee: Biochemtex S.p.A., Tortona (AL) (IT)

( * ) Notice: Subject to any disclaimer, the term of this patent is extended or adjusted under 35 U.S.C. 154(b) by 0 days.

(21) Appl. No.: 15/032,666

(22) PCT Filed: Oct. 31, 2014

(86) PCT No.: PCT/EP2014/002928
§ 371 (c)(1),
(2) Date: Apr. 28, 2016

(87) PCT Pub. No.: WO2015/062737
PCT Pub. Date: May 7, 2015

(65) Prior Publication Data
US 2016/0264499 A1      Sep. 15, 2016

(30) Foreign Application Priority Data
Oct. 31, 2013   (IT) .................................. 2013A0885

(51) Int. Cl.
C07C 29/132   (2006.01)
D21B 1/00     (2006.01)
D21B 1/02     (2006.01)
D21B 1/04     (2006.01)
D21B 1/06     (2006.01)
C07C 31/18    (2006.01)
C07C 31/27    (2006.01)

(52) U.S. Cl.
CPC ............... *C07C 29/132* (2013.01); *D21B 1/00* (2013.01); *D21B 1/02* (2013.01); *D21B 1/04* (2013.01); *D21B 1/06* (2013.01); *D21B 1/061* (2013.01); *C07C 31/18* (2013.01); *C07C 31/27* (2013.01)

(58) Field of Classification Search
None
See application file for complete search history.

(56) References Cited

U.S. PATENT DOCUMENTS

2010/0255983 A1   10/2010   Zhang
2010/0256424 A1   10/2010   Zhang et al.
(Continued)

FOREIGN PATENT DOCUMENTS

FR   WO 2012085362 A1 *   6/2012   ........... C07C 29/132

OTHER PUBLICATIONS

WO2012085362 A1, Jun. 28, 2012, pp. 1-10, English translation.*
(Continued)

*Primary Examiner* — Fereydoun G Sajjadi
*Assistant Examiner* — Medhanit Bahta
(74) *Attorney, Agent, or Firm* — Edwin A. Sisson, Attorney at Law, LLC; Jeffrey J. Banyas

(57) ABSTRACT

A process for producing polyols from a low viscosity slurry comprising a thermally treated ligno-cellulosic biomass which has been subjected to a fiber shives reduction step is provided. Specifically, a continuous process for catalyzing the formation of polyol products, such as ethylene glycol and propylene glycol, from the low viscosity slurry is provided.

30 Claims, 13 Drawing Sheets

(56) References Cited

U.S. PATENT DOCUMENTS

| | | |
|---|---|---|
| 2011/0312487 A1 | 12/2011 | Chen et al. |
| 2011/0312488 A1 | 12/2011 | Chen et al. |
| 2011/0313212 A1 | 12/2011 | Klanes et al. |
| 2012/0125324 A1 | 5/2012 | Fisk |
| 2013/0248767 A1 | 9/2013 | Ampulski et al. |

OTHER PUBLICATIONS

Zhang et al., "Catalytic conversion of cellulose into ethylene glycol over supported carbide catalysts", Catalysis Today, Sep. 30, 2009, pp. 77 to 85, vol. 147, No. 2, Elsevier BV, GB.*
Ji et al., "Direct catalytic conversion of cellulose into ethylene glycol using nickel-promoted tungsten carbide catalysts", Angewandte Chemie International Edition, Sep. 11, 2008, pp. 8510 to 8513, vol. 47, No. 44.*
Zhang et al., "A new 3D mesoporous carbon replicated from commercial silica as a catalyst support for direct inversion of cellulose into ethylene glycol", Chemical Communications, Dec. 8, 2009,, pp. 862 to 864, vol. 16, No. 6.*
Zheng et al., "Transition Metal-Tungsten Bimetallic Catalysts for the Conversion of Cellulose into Ethylene Glycol", Chemistry & Sustainability, Dec. 8, 2009, pp. 63 to 66, vol. 3, No. 1.*
Zhang et al., "A new 3D mesoporous carbon replicated from commercial silica as a catalyst support for direct conversion of cellulose into ethylene glycol", Chemical Communications, Dec. 8, 2009,, pp. 862 to 864, vol. 46, No. 6.
Elliott et al., "3.1.1.2 Feed Processing and Handling DL2 Final Report", Pacific Northwest National Laboratory, Sep. 2006.

* cited by examiner

WELDING ENGINEERS 30 mm SCREW ARRANGEMENT for 315-4350 except as noted, screws have 30.00 mm constant pitch and 29.72mm flight O.D.

| Item # | # Required | Name | Stem - root Dia(mm) - length (mm) |
|---|---|---|---|
| 1 | 1 | Main compounder screw | cyl - 24.36 - 45.01 |
| 2 | 1 | Aux " " | cyl - 24.36 - 45.01 |
| 3 | 2 | Main Feed Screw | tapered - 19.5 to 24.36 - 157.5 |
| 4 | 2 | Aux " " | tapered - 19.5 to 24.36 - 157.5 |
| 5 | 1 | Main Mill Screw | cyl - 24.36 - 157.5 |
| 6 | 1 | Aux Mill Screw | cyl - 24.36 - 157.5 |
| 7 | 2 | Main compounder screw | cyl - 28.60 - 45.01 (no flights) |
| 8 | 2 | Aux " " | cyl - 28.60 - 45.01 (no flights) |
| 9 | 2 | Main Mill Screw | cyl - 24.36 - 112.5 |
| 10 | 2 | Aux Mill Screw | cyl - 24.36 - 112.5 |
| 11 | 1 | Main compounder screw | cyl - 28.19 - 45.01 |
| 12 | 1 | Aux " " | cyl - 28.19 - 45.01 |
| 13 | 2 | Main Mill Screw | cyl - 22.86 - 157.5 (10.01 pitch) |
| 14 | 2 | Aux " " | cyl - 22.86 - 157.5 (10.01 pitch) |
| 15 | 1 | Main Mill Screw | cyl - 22.86 - 89.84 |
| 16 | 1 | Aux " " | cyl - 22.86 - 89.84 |
| 17 | 1 | Main Mill Screw | cyl - 22.86 - 157.5 |
| 18 | 1 | Aux Extruder Screw | cyl - 22.86 - 153.6 |
| 19 | 1 | Main Extruder Screw | cyl - 24.359 - 180.4 |
| 20 | 11 | Main Connection Stud | |
| 21 | 10 | Aux " " | |

| | screw segment item #'s; from feed | screw length (mm) |
|---|---|---|
| main | 1, 3, 5, 7, 3, 9, 11, 9, 13, 13, 7, 15, 17, 19 | 1620.1 |
| aux | 2, 4, 6, 8, 4, 10, 12, 10, 14, 14, 8, 16, 18 | 1436 |

CONVERSION OF A LOW VISCOSITY LIGNO-CELLULOSIC BIOMASS SLURRY INTO POLYOLS

PRIORITIES AND CROSS REFERENCES

This patent application claims the priority from International Application No. PCT/EP2014/002928 filed on 31 Oct. 2014 and Italian Patent Application No. TO2013A000885 filed on 31 Oct. 2013 the teachings of both of which are incorporated herein by reference in their entirety.

BACKGROUND

Polyols are valuable materials with uses such as PTA/PET, cold weather fluid, cosmetics and many others. Generating polyols from cellulose instead of olefins can be a more environmentally friendly and economically attractive process. Catalytic conversion of cellulose into ethylene glycol over supported carbide catalysts was disclosed in Catalysis Today, 147, (2009) 77-85. US 2010/0256424, and US 2010/0255983 teach a method of preparing ethylene glycol from cellulose and a tungsten carbide catalyst to catalyze the reaction. Tungsten carbide catalysts have also been published as successful for batch-mode direct catalytic conversion of cellulose to ethylene glycol in Angew. Chem. Int. Ed 2008, 47, 8510-8513 and supporting information. A small amount of nickel was added to a tungsten carbide catalyst in Chem. Comm. 2010, 46, 862-864. Bimetallic catalysts have been disclosed in ChemSusChem, 2010, 3, 63-66.

US2011/312487, US2011/312488, and US2011/0313212 describes conversion of cellulose to polyol using a process which involves contacting cellulose with a catalyst system in a reaction zone to generate an effluent stream comprising at least one polyol and recovering the polyol from the effluent stream. The effluent stream further comprises unreacted water and hydrogen and reaction intermediates which may be recycled to the reaction zone. The catalyst system comprises both an unsupported catalytic component and a supported catalytic component.

However, the above process does not describe the use of a ligno-cellulosic biomass, which up to know have presented problems as starting materials, primarily related to their highly viscous nature when presented as a slurry comprising solid ligno-cellulosic material and a carrier liquid. It has been documented that a solid presents significant handling problems, as described in PNNL-16079, September 2006, which states:

High-pressure feeding systems for biomass slurries have been recognized as a process development issue at least as long as the modern biomass conversion systems have been under development since the Arab oil embargo of 1973. The authors review the state of the art and various slurry pumping systems, the vast majority of which include ball check valves. Their conclusion is that high-pressure feeding remains a problem for small scale production but believe "the high-pressure feeding of biomass slurries should be more readily achieved at larger flow rates wherein the fibrous nature of the biomass would not be expected to bridge and plug the orifices and valves.

Thus, there exists a need to provide a low viscosity ligno-cellulosic biomass slurry composition which allows processing in a catalytic system for generating polyol. The mechanically thermally treated ligno-cellulosic biomass process described herein to produce a low viscosity ligno-cellulosic biomass slurry, as well as its subsequent conversion to polyol materials, also described herein, address this need.

SUMMARY

It is disclosed a process for converting a thermally treated ligno-cellulosic biomass comprising cellulose and lignin derived from a ligno-cellulosic feedstock into at least one polyol. The thermally treated ligno-cellulosic biomass is in the physical form of at least fibres, fines and fiber shives, wherein:
i. the fibres each have a width of 75 µm or less, and a fibre length greater than or equal to 200 µm,
ii. the fines each have a width of 75 µm or less, and a fine length less than 200 µm,
iii. the fiber shives each have a shive width greater than 75 µm with a first portion of the fiber shives each having a shive length less than 737 µm and a second portion of the fiber shives each having a shive length greater than or equal to 737 µm.

The process comprises the steps of:
a. reducing the fiber shives of the thermally treated ligno-cellulosic biomass, wherein the percent area of fiber shives having a shive length greater than or equal to 737 µm relative to the total area of fiber shives, fibres and fines of the thermally treated ligno-cellulosic biomass after fiber shives reduction is less than the percent area of fiber shives having a shive length greater than or equal to 737 µm relative to the total area of fiber shives, fibres and fines of the thermally treated ligno-cellulosic biomass before fiber shives reduction, wherein the percent area is measured by automated optical analysis;
b. dispersing an amount of the thermally treated ligno-cellulosic biomass before, during or after fiber shives reduction into an amount of a carrier liquid to create a slurry stream;
c. contacting in a reaction zone, hydrogen, water, and the slurry stream, with a catalyst system at reaction conditions to generate an effluent stream comprising the at least one polyol;
d. separating hydrogen from the effluent stream and recycling at least a portion of the separated hydrogen to the reaction zone;
e. separating water from the effluent stream and recycling at least a portion of the separated water to the reaction zone; and
f. recovering the at least one polyol from the effluent stream.

It is also disclosed that a part of the fiber shives reduction may be done by separating at least a portion of the fiber shives having a shive length greater than or equal to 737 µm from the thermally treated ligno-cellulosic biomass.

It is further disclosed that a part of the fiber shives reduction may be done by converting at least a portion of the fiber shives having a shive length greater than or equal to 737 µm in the thermally treated ligno-cellulosic biomass to fibres or fines.

It is also disclosed that at least a part of the fiber shives reduction step may be done by applying a work in a form of mechanical forces to the thermally treated ligno-cellulosic biomass, and all the work done by all the forms of mechanical forces on the thermally treated ligno-cellulosic biomass is less than 500 Wh/Kg per kg of the thermally treated ligno-cellulosic biomass on a dry basis.

It is further disclosed that all the work done by all the forms of mechanical forces on the thermally treated ligno-cellulosic biomass may be less than a value selected from the group consisting of 400 Wh/Kg, 300 Wh/Kg, 200 Wh/Kg, 100 Wh/Kg, per kg of the thermally treated ligno-cellulosic biomass on a dry basis.

It is also disclosed that the mechanical energy applied to the thermally treated ligno-cellulosic biomass may be not mechanical energy derived from free-fall or gravity mixing.

It is also disclosed that the mechanical forces may be applied using a machine selected from the group consisting of single screw extruders, twin screw extruders, and banburies.

It is further disclosed that the slurry stream may have a viscosity less than a value selected from the group consisting of 0.1 Pa s, 0.3 Pa s, 0.5 Pa s, 0.7 Pa s, 0.9 Pa s, 1.0 Pa s, 1.5 Pa s, 2.0 Pa s, 2.5 Pa s, 3.0 Pa s, 4 Pa s, 5 Pa s, 7 Pa s, 9 Pa s, 10 Pa s, wherein the viscosity is measured at 25° C., at a shear rate of 10 s$^{-1}$ and at a dry matter content of 7% by weight of the slurry stream It is also disclosed that the dry matter content of the slurry stream by weight may be greater than a value selected from the group consisting of 5%, 7%, 8%, 10%, 12%, 15%, 18%, 20%, 25%, 30%, 35%, and 40%.

It is further disclosed that the percent area of the fiber shives having a shive length greater than or equal to 737 µm relative to the total area of fiber shives, fibres and fines of the thermally treated ligno-cellulosic biomass after fiber shives reduction may be less than a value selected from the group consisting of 1%, 0.5%, 0.25%, 0.2% and 0.1%.

It is also disclosed that the slurry stream may not contain ionic groups derived from added mineral acids, mineral bases, organic acids, or organic bases.

It is further disclosed that the thermally treated ligno-cellulosic biomass may have been steam exploded before fiber shives reduction.

It is also disclosed that the process may comprise the step of adding a hydrolysis catalyst to the slurry to hydrolyze at least a portion of the cellulose to glucose.

It is further disclosed that the catalyst system may comprise an unsupported component comprising a compound selected from the group consisting of a tungsten compound, a molybdenum compound, and any combination thereof, and a supported component comprising a supported active metal component selected from the group consisting of Pt, Pd, Ru, Rh, Ni, Ir, and combinations thereof on a solid catalyst support.

It is also disclosed that the catalyst system may comprise a metal component selected from the group consisting of IUPAC Groups 4, 5 and 6 of the Periodic Table, the metal component having an oxidation state greater than or equal to 2+ wherein the metal component is in a form other than a carbide, nitride or phosphide, and a hydrogenation component selected from the group consisting of IUPAC Groups 8, 9, and 10, of the Periodic Table.

It is also disclosed that the conversion of the at least a carbohydrate in the slurry stream to the at least one polyol may be operated in a mode selected from the group consisting of batch mode operation and continuous mode operation It is further disclosed that the process may further comprise separating at least one co-product from the effluent stream and recycling at least a portion of the separated co-product to the reaction zone.

It is also disclosed that the effluent stream may further comprise cellulose and the process further comprises separating the cellulose from the effluent stream and recycling at least a portion of the separated cellulose to the reaction zone.

It is further disclosed that the effluent stream may further comprise at least a portion of the catalyst system, said process further comprising separating at least a portion of the catalyst from the effluent stream and recycling separated catalyst to the reaction zone.

It is also disclosed that the process may further comprise reactivating the separated catalyst prior to recycling the catalyst to the reaction zone.

It is further disclosed that the catalyst system may be separated from the effluent stream using a technique selected from the group consisting of direct filtration, settling followed by filtration, hydrocyclone, fractionation, centrifugation, the use of flocculants, precipitation, liquid extraction, evaporation, and combinations thereof.

It is also disclosed that at least a portion of the catalyst system may be separated from the effluent stream after the hydrogen is separated from the effluent stream, and before the water is separated from the effluent stream.

It is further disclosed that the reaction zone may comprise a mixing zone upstream of a reactor and wherein the separated hydrogen is recycled to the reactor and the separated water is recycled to the mixing zone.

It is also disclosed that the reaction zone may comprise a mixing zone upstream of a reactor and wherein at least a portion of the separated at least one co-product is recycled to the reactor, the mixing zone, or both.

It is further disclosed that the hydrogen may be separated from the effluent stream before the water is separated from the effluent stream.

It is also disclosed that the at least one co-product may be separated after the hydrogen and the water are separated from the effluent stream.

It is further disclosed that the at least one co-product may be selected from the group consisting of alcohols, organic acids, aldehydes, monosaccharides, polysaccharides, phenolic compounds, hydrocarbons, glycerol, depolymerized lignin, carbohydrates, and proteins.

It is also disclosed that the reaction zone may comprise at least a first input stream and a second input stream, the first input stream comprising at least the feedstock comprising cellulose and the second input stream comprising hydrogen.

It is further disclosed that the first input stream may be pressurized prior to the reaction zone and the second input stream is pressurized and heated prior to the reaction zone.

It is also disclosed that wherein the first input stream may be pressurized and heated to a temperature below the decomposition temperature of the cellulose prior to the reaction zone and the second input stream is pressurized and heated prior to the reaction zone.

It is further disclosed that the first input stream and the second input stream may further comprise water.

It is also disclosed that the reaction zone may comprise a system selected from the group consisting of an ebullating catalyst bed reaction system, an immobilized catalyst reaction system having catalyst channels, an augured reaction system, a fluidized bed reaction system, a mechanically mixed reaction system, and a slurry reactor system.

It is further disclosed that the at least one polyol may comprise a compound selected from ethylene glycol and propylene glycol, or a mixture thereof.

BRIEF DESCRIPTION OF THE DRAWING

FIG. 1 is the screw design of the twin screw extruder used in the experiments.

DETAILED DESCRIPTION

Figure 2:
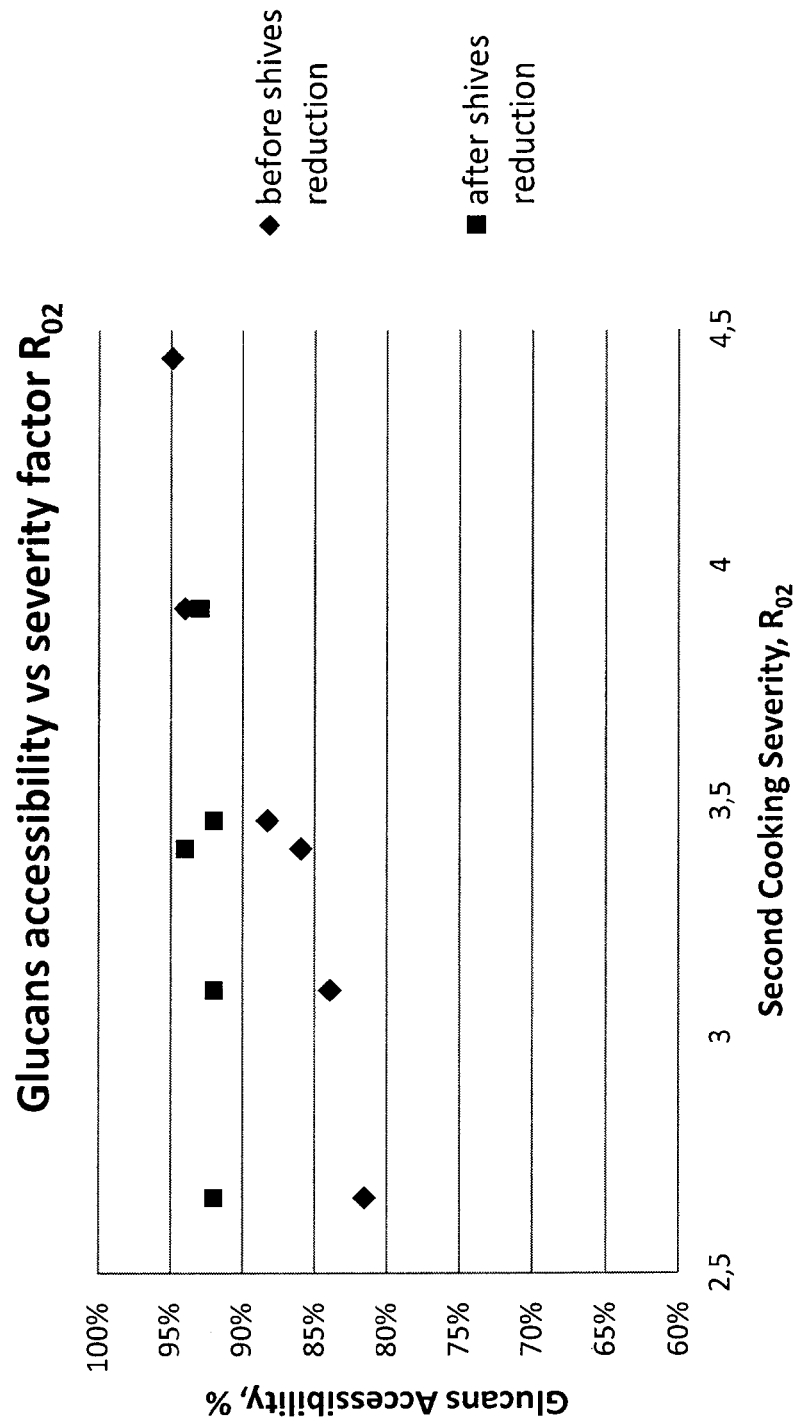
FIG. 2 depicts the glucans accessibility of thermally treated ligno-cellulosic biomass before and after fiber shives reduction at various severity factors of thermal treatment.

The described process utilizes the discovery that a thermally treated ligno-cellulosic biomass comprising cellulose can be almost immediately converted to a low viscosity slurry by means of a fiber shives reduction step, specifically by reducing the amount of long shives in the thermally treated ligno-cellulosic biomass.

Inventors discovered that the low viscosity slurry comprising the thermally treated ligno-cellulosic biomass which has been subjected to a fiber shives reduction step can be converted with improved efficiency to a polyols mixture, by contacting the low viscosity slurry with hydrogen and a heterogeneous catalyst system.

It is known in the paper and pulp industry that ligno-cellulosic biomass feedstocks are characterized by the content of its particles classified into fibres, fines and fiber shives. Fibres are measured on the basis of their 2 dimensional profile with fibres having a width of 75 µm or less, and a fibre length greater than or equal to 200 µm. Fines are those particles having a width of 75 µm or less, and a fines length less than 200 µm. Geometrically, one can think of a fine as a fibre which has been cut in length. Fiber shives have a shive width greater than 75 µm and can be any length. For the purpose of this specification the shive length can be categorized with a first portion of the fiber shives having a shive length less than 737 µm and a second portion of the fiber shives having a shive length in the range of greater than or equal to 737 µm. Because the width and length describe high aspect ratio particles, the width is less than the length, except in the special case of the circle or square. In the special case when the length and width equal each other the practitioner selects one measurement as the length and arbitrarily therefore, the other measurement as the width.

The 737 µm is selected on the basis of classification of the particle distribution determined by the instrument used in the experiments which gave rise to the disclosed discovery. The sizes of the particles were grouped, with one of the groups having a range of 737-1138 µm. The next group had 1138 as its minimum size. From these groups the graphs were made in figures and determinations made about the effective ranges needed to practice the discovery.

Dimensions of Common NonWood Fibers cited in the Kirk-Othmer Encyclopedia of Chemical Technology, fifth edition, are

| Fibre Source | Mean Length, µm | Mean Diameter, µm | L/D ratio |
| --- | --- | --- | --- |
| Rice straw | 1410 | 8 | 175 |
| Wheat straw | 1480 | 13 | 110 |
| Corn stalk | 1260 | 16 | 80 |
| Cotton stalk | 860 | 19 | 45 |
| Cotton liners | 3500 | 21 | 165 |
| Sugarcane bagasse | 1700 | 20 | 85 |
| Hemp | 20000 | 22 | 1000 |
| Kenaf bast | 2740 | 20 | 135 |
| Kenaf core | 600 | 30 | 20 |
| Seed flax | 27000 | 16 | 1250 |
| Bamboo | 2700 | 14 | 190 |
| Papyrus | 1500 | 12 | 125 |
| Softwood | 3000 | 30 | 100 |
| Hardwood | 1250 | 25 | 50 |

As evident, the average fibre width, as previously defined, is less than or equal to 75 µm.

It is generally viewed that the fiber shives are not a single fibre having the width greater than 75 µm, but bundle of fibres or fibre tangles which combined exhibit a width greater than 75 µm.

This invention is based upon the discovery it is the fiber shives in thermally treated ligno-cellulosic biomass which are responsible for the long enzymatic hydrolysis times, high initial viscosity of slurries from the thermally treated ligno-cellulosic biomass, and the lowered glucose recoveries and yields. This specification demonstrates that by reducing the amount (percentage) of the fiber shives in the thermally treated ligno-cellulosic biomass, the viscosity of the material in a slurry drops dramatically, and there is a significant improvement in sugar yields and recovery during fermentation.

The ability to characterize and fines, fibres and fiber shives is well known in the art and the subject of many industrial standards such as those found in the fiber characterization standards used for all the fiber characterization work in this specification.

Because fiber shives are bundles of fibres, they can be reduced in many ways. First, at least a part of the fiber shives can be removed or separated from the thermally treated ligno-cellulosic biomass. Separation techniques of fiber shives from fibres and fines is well known in the art of natural fibres (e.g. cotton, flax, and others) and also in the paper and pulp industry. Non-limiting examples are the cotton gin and wool carding apparata. Again, not limiting, the separation can occur by bulk density separation, a vibrating bed where the fiber shives separate from the fines and fibres, air elutriation, or even screening, sieving or cyclones. After separation, the fiber shives can be further processing into fibres or fines, and recombined with the thermally treated ligno-cellulosic biomass or re-fed into the thermal treatment process.

The fiber shives can also be reduced by converting them to another form. One method of converting the fiber shives is to apply mechanical forces to the thermally treated ligno-cellulosic biomass to convert the fiber shives to fibres and/or fines. An important consideration is that the difference between a fine and a fibre is the length, as both have a width of less than or equal to 75 μm. The application of mechanical forces to thermally treated ligno-cellulosic biomass is practiced in the art, but always under the belief that the fibres (less than or equal to 75 μm width) must be acted upon. By focusing the application of the mechanical forces upon the fiber shives which are bundles of fibres>75 μm, the amount of work needed is to obtain the benefits mentioned earlier is significantly less than prior art disclosures.

The reason for this reduced work requirement is analogized to yarn which is twisted fibres. It does not take much energy to pull apart a ball of tangled yarn, but it takes much more energy to actually destroy and pull apart the twisted yarn fibre.

The start of the process is the feedstock of thermally treated ligno-cellulosic biomass feedstock. The type of ligno-cellulosic biomass feedstock for the thermal treatment is covered in the feedstock selection section.

In typical conversion of ligno-cellulosic biomass feedstock to ethanol, the ligno-cellulosic biomass is thermally treated prior to enzymatic hydrolysis. Oftentimes this thermal treatment will include acids or bases to increase the liquefaction rate and reduce the hydrolysis time. In many cases the thermal pretreatment includes a steam explosion step.

The thermal treatment is measured by a severity factor which is a function the time and temperature of the thermal treatment. A preferred thermal treatment is described in the thermal treatment section of this specification.

The more time of heat exposure, the more the severe the treatment. The higher the temperature of exposure, the more the severe the treatment. The details of calculating the severity factor for this invention are described later. Steam explosion severity factor ($R_{02}$) is taken as the reference severity factor. However, conventional wisdom holds that the more severe the treatment, the more surface area and cells of the ligno-cellulosic biomass are exposed to enzymes for hydrolysis or further treatment. This is demonstrated in FIG. 2, showing that the glucans become more accessible as the severity factor increases.

Figure 3:
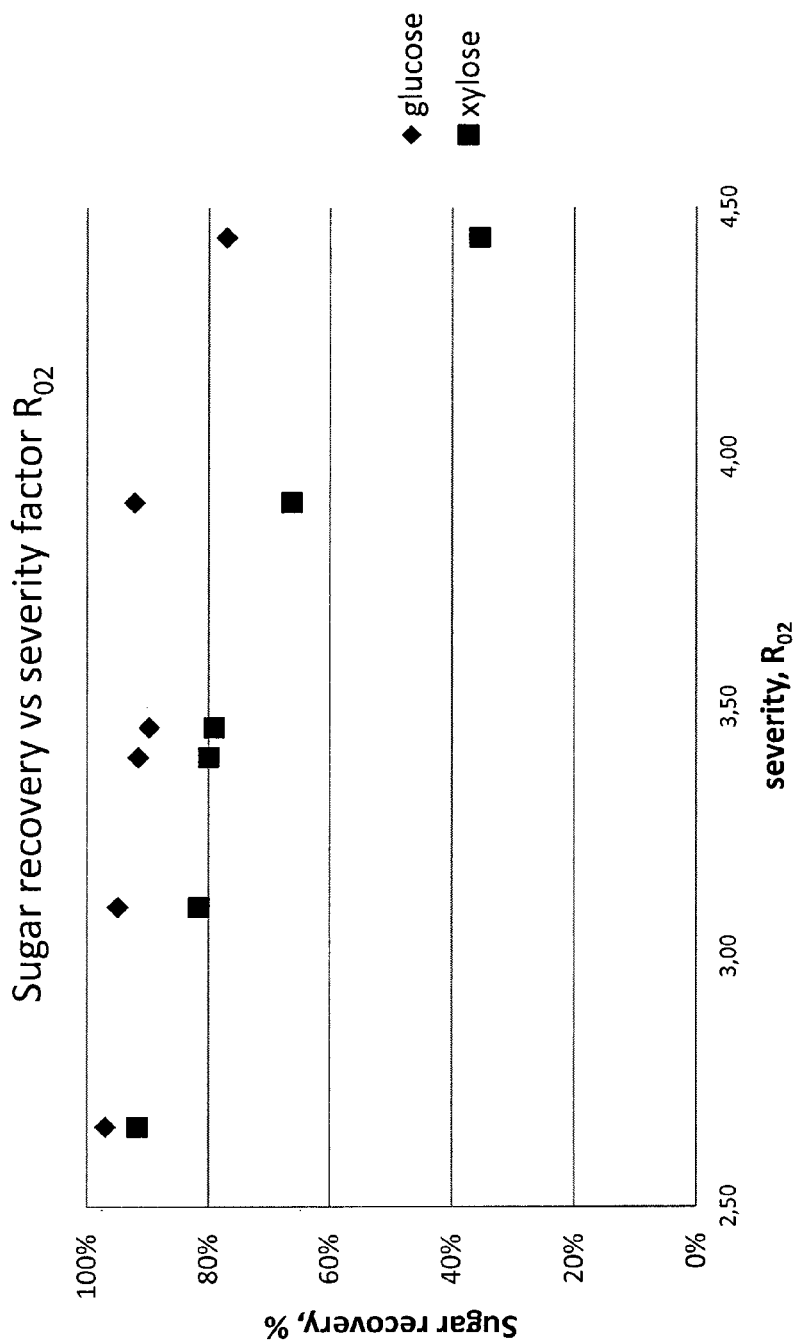
FIG. 3 depicts the glucose and xylose recovery of thermally treated ligno-cellulosic biomass before and after fiber shives reduction at various severity factors of thermal treatment.

However, as demonstrated in FIG. 3, the amount of glucose and xylose that may be recovered relative to the amount present before the thermal treatment declines at higher severity factors. It is believed that the higher temperature converts or otherwise destroys the sugars. Thus, while the sugars existing in the thermally treated ligno-cellulosic biomass become more available, less sugars exist after severe thermal treatment because the severe temperature/time converts them to sugars degradation products, such as furfural and HMF.

Taking for example, FIG. 3, the points at severity factor 2.66, 97% of the glucose is present after the thermal treatment. In contrast, at a severity factor of 4.44 only 77% is recoverable, or alternatively 23% is destroyed. For xylose, almost 64% is destroyed. However, looking at FIG. 2, for the severity factor of 2.66, only 82% of the glucans are accessible or able to be converted to glucose. Thus, while 97% of the starting amount still exists, only 82% of that can be enzymatically converted. Looking at FIG. 2, severity factor 4.44, 95% of the glucans are accessible but remember from FIG. 3, that only 82% of the starting amount of glucans remains.

What has been discovered is that these inaccessible glucans reside in the fiber shives. When the biomass is processed it is often reduced to width and length that conform to fibres—high aspect ratio as defined in the standard. Usually the thermal treatment of the ligno-cellulosic biomass will create a thermally treated ligno-cellulosic biomass in the physical forms of at least fibres, fines and fiber shives. These physical forms are well known according the definitions described earlier.

Figure 4:
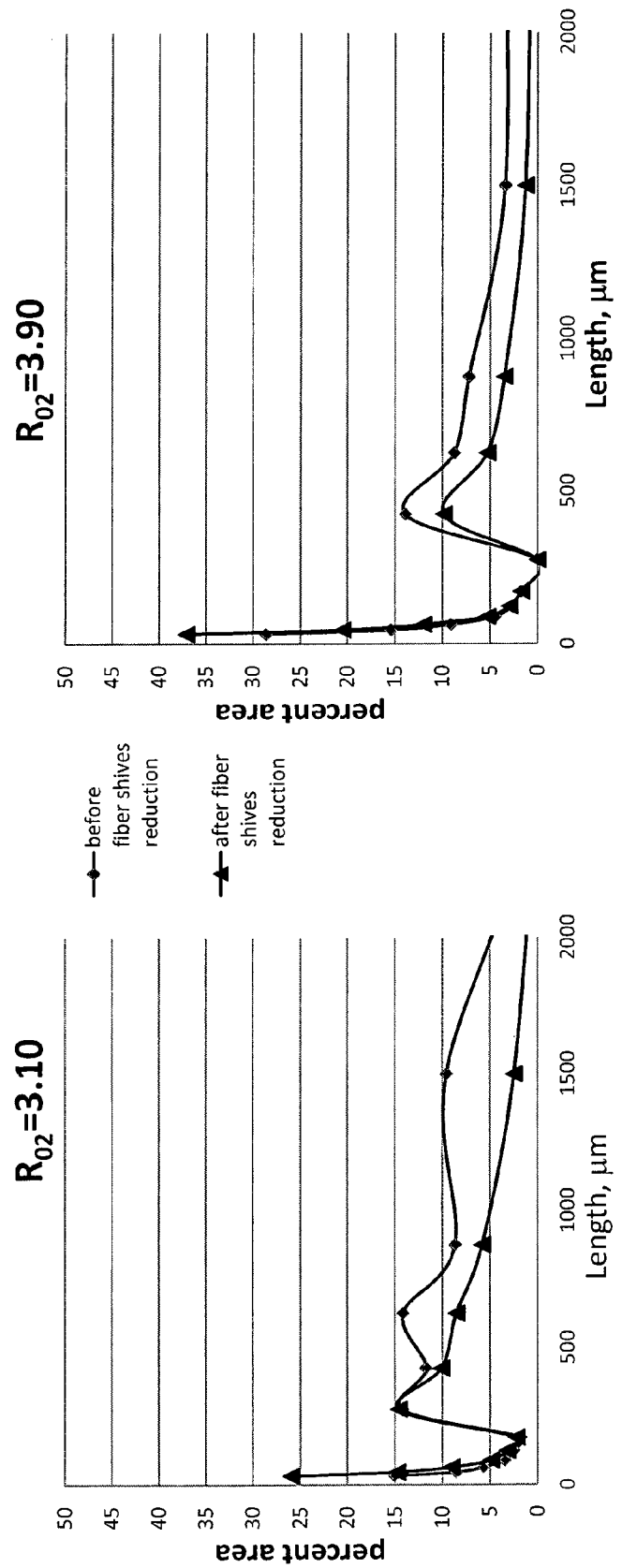
FIG. 4 is fibres and fines distribution of thermally treated ligno-cellulosic biomass before and after fiber shives reduction at two severity factors of thermal treatment.

The fines and fibres (not shives) distribution of thermally treated ligno-cellulosic biomass is shown in FIG. 4. FIG. 4*a*) shows the percent area of each length class relative to the total area of fines, fibres and fiber shives for the severity factor $R_{02}$ of 3.1. When the severity factor is increased to 3.91, (FIG. 4*b*), it is evident that the percent area of fines has increased (particles of length<200 μm) and the percent area of fibres longer than or equal to 737 μm is reduced. The same considerations hold in the case that population of fines and fibres are considered.

The plots and graphs also show the measurements of the thermally treated ligno-cellulosic biomass after fiber shives reduction, which in this case was passing it through a twin screw extruder at about 35% dry matter content having the screw element design of FIG. 1. The twin screw extruder is also known as a mechanical treatment or the application of mechanical forces on the thermally treated ligno-cellulosic biomass. One of ordinary skill could easily obtain this design from the manufacturer listed.

The dominant role of the fiber shives is evidenced by seeing that first, according to FIG. 4, the thermally treated ligno-cellulosic biomass after fiber shives reduction through the extruder has a reduced percent area of long fibres for both the low and high severity factors of 3.1 and 3.91. However, for the low severity factor of 3.1, the conversion of fiber shives improved the glucan accessibility from 84 to 93 percent (FIG. 2). Again, the same considerations hold in the case that population of fibres and fiber shives are considered. While at the high severity of 3.91, there was substantially no improvement in the glucan accessibility. Were the long fibres responsible for accessibility, the accessibility of the glucans for the thermally treated ligno-cellulosic biomass should have been less than 94% and the reduction of the percent area of long fibres (or equivalently the population of long fibres) during the extrusion (application of mechanical forces) should have caused an increase in the accessibility. The accessibility did not increase establishing that it is not the conversion of fibres to fines that causes the increased accessibility.

Figure 5:
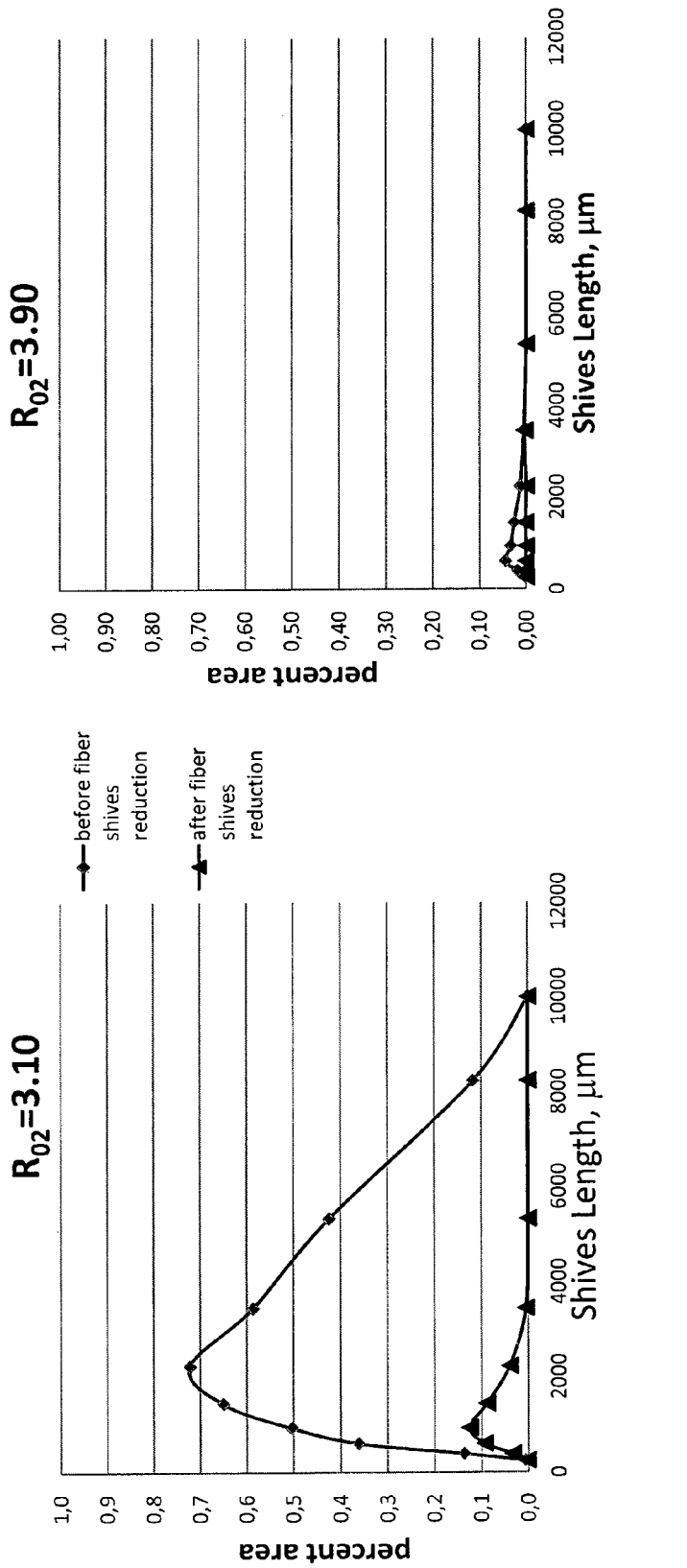
FIG. 5 is the fiber shives distribution of thermally treated biomass before shives reduction and the thermally treated biomass after shives reduction at two severity factors of thermal treatment.
Figure 6:
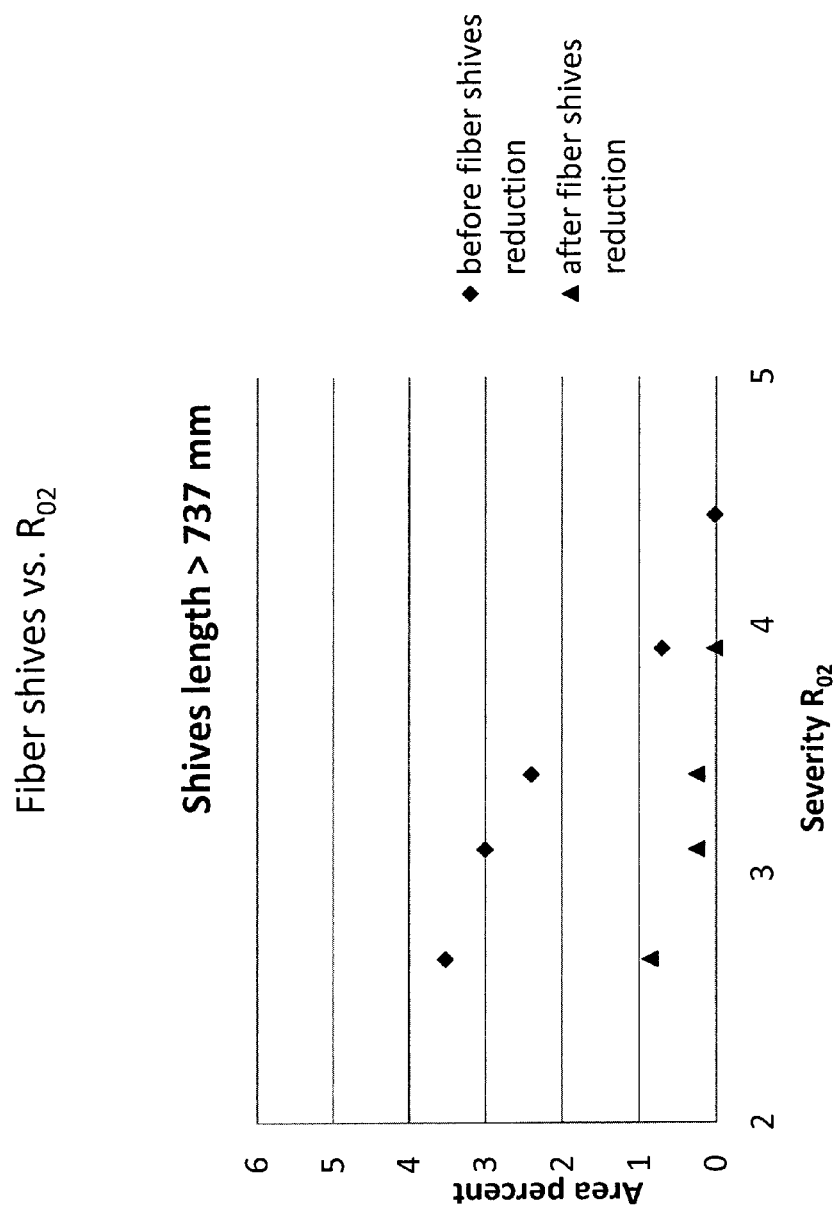
FIG. 6 is the fiber shives content of thermally treated ligno-cellulosic biomass before and after fiber shives reduction as a function of the severity factor of thermal treatment.

The role of the fiber shives is shown in FIG. 5, which contains the percent area distribution of fiber shives of two samples prepared at low severity factor ($R_{02}$=3.10, FIG. 5*a*) and high severity factor ($R_{02}$=3.90, FIG. 5*b*), before fiber shives reduction and after fiber shives reduction. The sample at low severity before fiber shives reduction contains a remarkable amount of fiber shives and the mechanical treatment reduces the amount of fiber shives in the sample at low severity, while the sample at high severity has already a small amount of fiber shives before fiber shives reduction. FIG. 6 reports the total percent area of fiber shives having a fiber shives length greater than 737 μm. The percent area of fiber shives of the sample at low severity is reduced from 3.5% to less than 1% by the fiber shives reduction. However, for the high severity thermally treated ligno-cellulosic biomass, fiber shives percent area is already less than 1% before fiber shives reduction. Thus, there is the conclusion that once the fiber shives are below a certain threshold, their removal does not impact the properties in a measurable way. Therefore, the percent area of the fiber shives having a shive length greater than or equal to 737 relative to the total area of fiber shives, fibres and fines of the thermally treated ligno-cellulosic biomass before fiber shives reduction is greater than a value selected from the group consisting of 1%, 2%, 3% and 4% and the percent area of the fiber shives having a shive length greater than or equal to 737 µm relative to the total area of fiber shives, fibers and fines of the thermally treated ligno-cellulosic biomass after fiber shives reduction is less than a value selected from the group consisting of 1%, 0.5, 0.25%, 0.02%, and 0.1%.

In a preferred embodiment, the percent area of the fiber shives having a shive length greater than or equal to 737 µm relative to the total area of fiber shives, fibers and fines of the thermally treated ligno-cellulosic biomass after fiber shives reduction is greater than 0, and less than a value selected from the group consisting of 1%, 0.5, 0.25%, 0.02%, and 0.1%, that is some long fiber shives are still present in the thermally treated ligno-cellulosic biomass after fiber shives reduction.

The total area of fiber shives, fibres and fines is measured using automated optical analysis which determines the area of the fiber shives, the area of the fibres and the area of fines. The proper machine, as described in the experimental section, will often provide the area of each individual class, as well as the area of each class as a percent of the total area of the sum of the classes. In the event the machine does not do the math, one of ordinary skill should be able to calculate the percent area knowing the areas, or the area knowing the total area and percent of each class measured.

In any event, the effect of the shives reduction should be such that the percent area of the fiber shives having a shive length greater than or equal to 737 µm relative to the total area of fiber shives, fibres and fines of the thermally treated ligno-cellulosic biomass after fiber shives reduction is less than a value selected from the group consisting of 5%, 10%, 20%, 30%, 40%, 50%, 60% and 70% of the percent area of the fiber shives having a shive length greater than or equal to 737 µm relative to the total area of fiber shives, fibres and fines of the thermally treated ligno-cellulosic biomass before fiber shives reduction.

Because the fiber shives are comprised of fibre bundles and agglomerated fibres, a reduced amount of energy is needed as compared to the prior art. As described in the experimental section only 0.1 to 0.2 Kw-h/kg on a wet basis or 0.25 to 0.50 Kw-h/kg on a dry matter basis was used to achieve the effects. Thus the preferred amount of work, or energy, imparted to the thermally treated ligno-cellulosic biomass is preferably less than a number selected from the group consisting of 500 Wh/Kg, 400 Wh/Kg, 300 Wh/Kg, 200 Wh/Kg, 100 Wh/Kg, per kg of the thermally treated ligno-cellulosic biomass on a dry basis. It is preferable that at least a part of the fiber shives reduction is done by applying mechanical forces to the thermally treated ligno-cellulosic biomass, and all the work applied in form of mechanical forces on the thermally treated ligno-cellulosic biomass is less than 500 Wh/Kg per kg of the thermally treated ligno-cellulosic biomass on a dry basis. It is even more preferable that all the work done by all the forms of mechanical forces on the thermally treated ligno-cellulosic biomass is less than a value selected from the group consisting of 400 Wh/Kg, 300 Wh/Kg, 200 Wh/Kg, 100 Wh/Kg, per kg of the thermally treated ligno-cellulosic biomass on a dry basis.

The application of mechanical forces to the thermally treated ligno-cellulosic biomass should be a mechanical process or sub-processes which applies work to the thermally treated ligno-cellulosic biomass and reduces the number of fiber shives longer than or equal to 737 µm during the fiber shives reduction. Mechanical forces applying work are distinct from chemical processes which may dissolve the fiber shives, for example. The type of forces or work applied as a mechanical force is shear, compression, and moving. It should be appreciated that the mechanical treatment may be a conversion process where the application of mechanical forces converts at least a portion of the fiber shives in the thermally treated ligno-cellulosic biomass to fibres or fines that remain part of the output. One class of machines for applying this type of work in a mechanical manner are those machines which apply shear such as an extruder, a twin screw extruder, a co-rotating extruder, a counter-rotating twin screw extruder, a disk mill, a bunbury, a grinder, a rolling mill, a hammer mill.

Preferably, the mechanical energy applied to the thermally treated ligno-cellulosic biomass is not mechanical energy derived from free-fall or gravity mixing.

In any case, it is noted the amount of work applied to the thermally treated ligno-cellulosic biomass for a given amount of time should be greater than the amount of work that can be provided by the forces of gravity or free fall mixing in that same period. One way to measure this is to consider the period of time in which the fiber shives are reduced to be the called fiber shives reduction time. The amount of work applied to the thermally treated ligno-cellulosic biomass during the fiber shives reduction time is preferably greater than the amount of work which can be applied to the thermally treated ligno-cellulosic biomass by free fall mixing or gravity. One embodiment will have no work applied in the form of free fall mixing or gravity during the shives reduction.

The fiber shives reduction time is preferably in the range of 0.1 to 30 minutes. While the fiber shives reduction time can be any positive amount less than 12 hours, less than 6 hours is more preferable, with less than 3 hours even more preferred and less than 1 hour more preferred, and less than 30 minutes being more preferable with less than 20 minutes being most preferred. In the case of an extruder, the preferred fiber shives reduction time is in the range of 0.1 to 15 minutes.

One of ordinary skill knowing that the forces are to be applied to fibre shives which on the average are 2 to 5 times the width of the fibre (less than or equal to 75 µm, averaging of 30-40 µm versus the fiber shives of 130-180 µm width) can easily adjust the apparatus. The twin screw extruder applies mechanical work in the forms of shear, compression and movement down the barrel of the screw. For a twin screw extruder one keeps the flights and distances further apart, as tighter distances applying forces to fibres are only wasted. In the experiments conducted in this specification, a conventional twin screw extruder for PET resins was used with no special screw as described in the prior art. For mills or blades, one sets the distance between the two parts creating the force for the particles having width of 130-180 not the particles less than or equal to 75 µm.

The simplest example of these machines are grist mills where two stones are rotated with a space between them. The space between the stones sets the size. One of ordinary skill would set the stones a distance apart to apply the force to particles having a width of >75 µm, with the fibres having a width of less than 75 µM passing between the stones with little or no work applied to these smaller particles. A disk mill is of the similar operation as it is the space between the disks which sets the application of the force.

Figure 7:
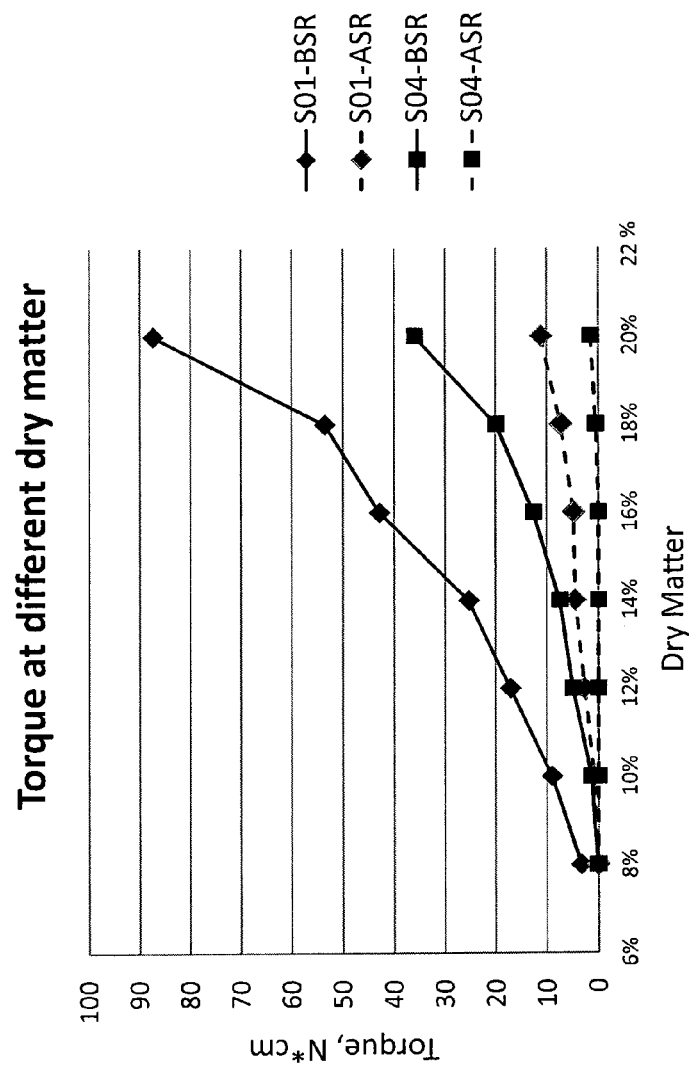
FIG. 7 plots the torque of slurries of various experimental runs at different dry matter contents in the slurry.

An additional feature it has been discovered, that once the fiber shives level is low enough, the thermally treated ligno-cellulosic biomass after fiber shives reduction will have much lower viscosity than the thermally treated ligno-cellulosic biomass when both are made into a slurry of water at the same dry matter content. FIG. 7 demonstrates this, at 20% dry matter the S01 (produced at a steam explosion severity factor of 2.66)) thermally treated material before fiber shives reduction needed a torque of 87 N-cm, while the thermally treated ligno-cellulosic biomass after shives reduction, needed only 11 N-cm.

Figure 8:
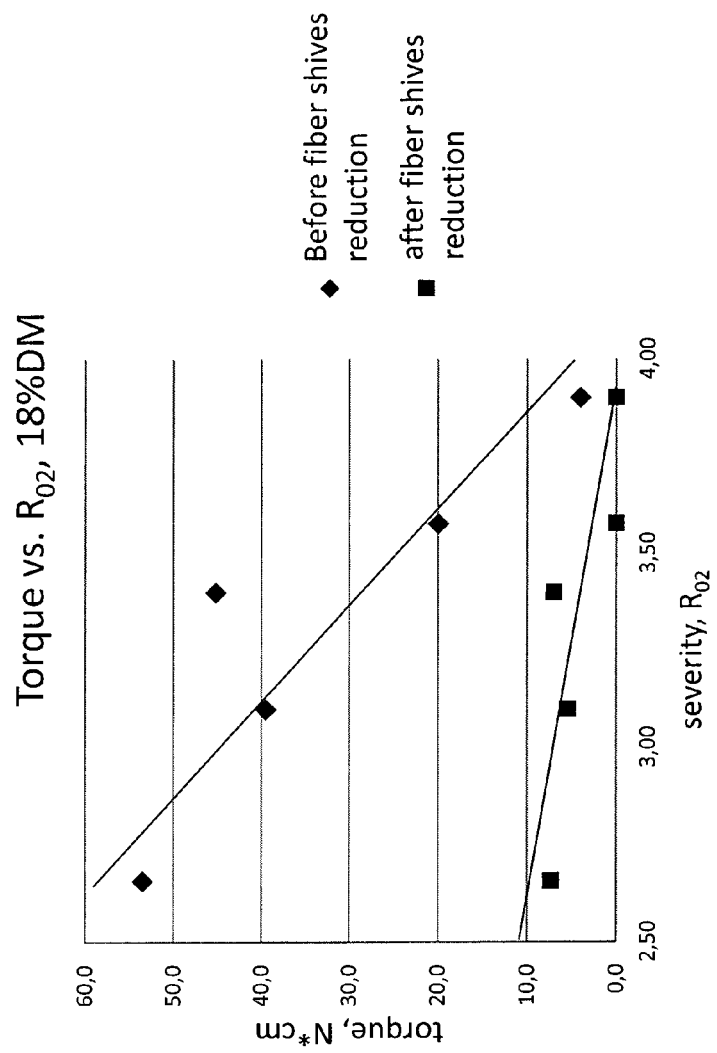
FIG. 8 plots the torque of slurries made from 18% dry matter content of the thermally treated ligno-cellulosic biomass before and after fiber shives reduction as a function of the severity factor of thermal treatment.

FIG. 8 shows the torque needed to agitate a slurry at 18% dry matter of thermally treated materials prepared at different severity factor, before and after fiber shives reduction. The torque decreases by increasing the severity factor, as the samples at low severity factor contain a bigger amount of fiber shives (FIG. 6). For each thermally treated material, the torque decreases by reducing the fiber shives by means of a mechanical treatment, but the effect is remarkably more evident in samples at low severity factor, which contains more fiber shives.

This slurry effect is especially critical as it can be can be done without hydrolysis, meaning that the low viscosity stream can be passed over an immobilized enzyme bed for enzymatic hydrolysis, or passed over a ion exchange resin for cationic exchange and subsequent "acid" hydrolysis.

Figure 10:
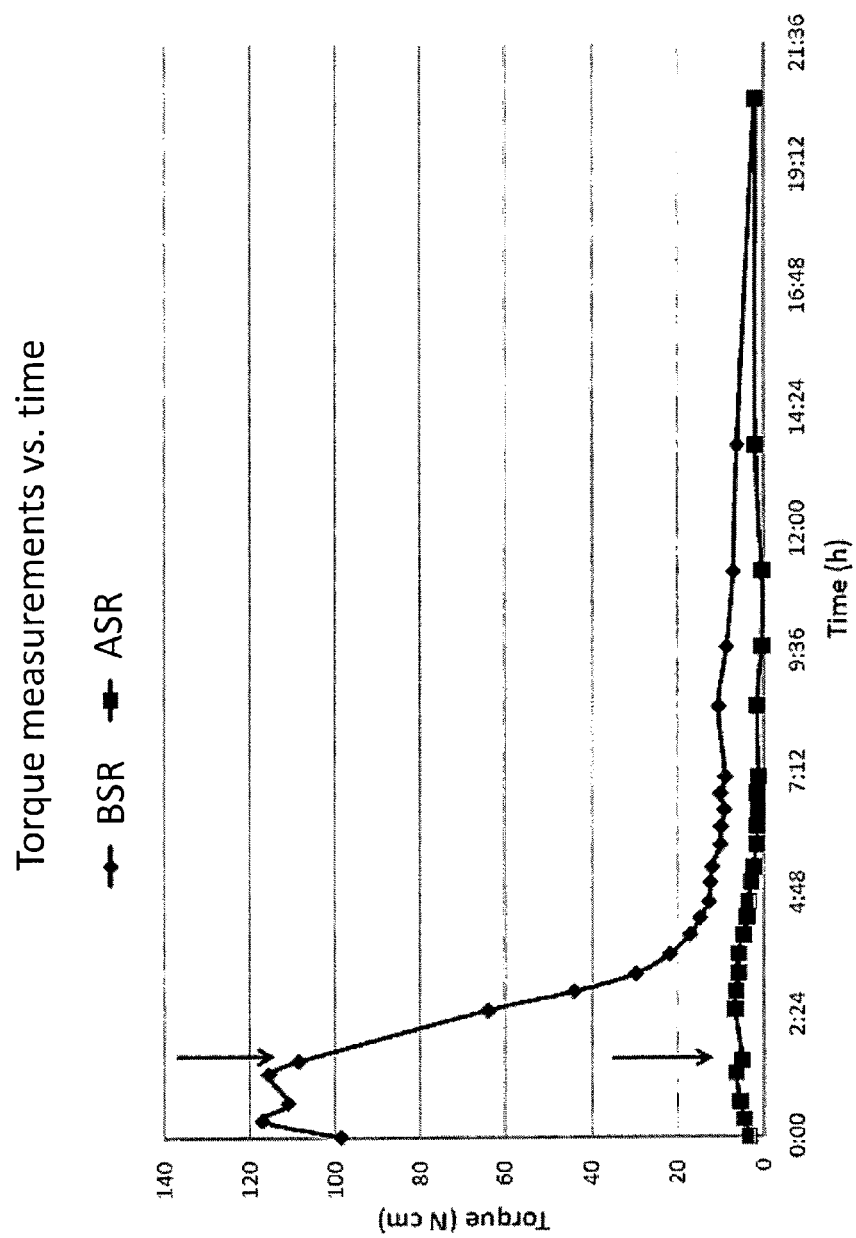
FIG. 10 plots the torque measurement versus time of thermally treated ligno-cellulosic biomass before and after fiber shives reduction.

This property is especially useful when exposing the material to enzymatic hydrolysis. In FIG. 10, the thermally treated ligno-cellulosic biomass before fiber shives reduction and the thermally treated ligno-cellulosic biomass after shives reduction were "slurried" into water with enzymes added at the arrow. It took 2+ hours after the enzymes were added for the viscosity of the thermally treated ligno-cellulosic biomass before fiber shives reduction to approach that of the thermally treated ligno-cellulosic biomass after fiber shives reduction. Thus, the process can be further characterized in that the output of thermally treated ligno-cellulosic biomass after fiber shives reduction is characterized by having a viscosity of a slurry of the thermally treated ligno-cellulosic biomass after fiber shives reduction in water less than the viscosity of a slurry of the thermally treated ligno-cellulosic biomass before fiber shives reduction in water, wherein the viscosities are measured at 25° C., at a shear rate of 10 $s^{-1}$ and at a dry matter content of 7% by weight of each slurry.

The process can be further characterized in that the thermally treated ligno-cellulosic biomass after fiber shives reduction is characterized by having a viscosity of a slurry of the thermally treated ligno-cellulosic biomass after fiber shives reduction in water less than a value selected from the group consisting of 0.1 Pa s, 0.3 Pa s, 0.5 Pa s, 0.7 Pa s, 0.9 Pa s, 1.0 Pa s, 1.5 Pa s, 2.0 Pa s, 2.5 Pa s, 3.0 Pa s, 4 Pa s, 5 Pa s, 7 Pa s, 9 Pa s, 10 Pa s, wherein the viscosity is measured at 25° C., at a shear rate of 10 $s^{-1}$ and at a dry matter content of 7% by weight of the slurry of the thermally treated ligno-cellulosic biomass after fiber shives reduction in the water.

The process can further comprise a slurry step, wherein the thermally treated ligno-cellulosic biomass before, during or after fiber shives reduction is dispersed into a liquid carrier, preferably comprising water or aqueous, to create a slurry stream. The slurry stream preferably has a viscosity less than a value selected from the group consisting of 0.1 Pa s, 0.3 Pa s, 0.5 Pa s, 0.7 Pa s, 0.9 Pa s, 1.0 Pa s, 1.5 Pa s, 2.0 Pa s, 2.5 Pa s, 3.0 Pa s, 4 Pa s, 5 Pa s, 7 Pa s, 9 Pa s, 10 Pa s, wherein the viscosity is measured at 25° C., at a shear rate of 10 $s^{-1}$ and at a dry matter content of 7% by weight of the slurry stream. The slurry stream will preferably have a dry matter content less than 100% but greater than a value selected from the group consisting of 5%, 7%, 8%, 10%, 12%, 15%, 18%, 20%, 25%, 30%, 35%, and 40%.

Because this slurry stream having this viscosity can be made without the use of hydrolysis catalysts such as enzymes, acids or bases, thus, the inventors have discovered an entirely new article of manufacture which is a slurry comprising water, soluble sugars, solid lignin, solid cellulose, which has a dry matter content in the range of 20 to 80% by weight of the total amount of the slurry and is void of or substantially void of a hydrolytic catalyst such as an enzyme or enzymes. Other preferable ranges of dry matter range are 25 to 80% by weight, with 30 to 80% by weight even more preferable. In some instances the dry matter range will have an upper limit of 70% by weight, with 60% less preferable and 40% even less preferable.

The torque of the slurry comprising the thermally ligno-cellulosic biomass after fiber shives reduction at 10 minutes after the addition of the solvent is less than the torque of a mixture of the thermally treated ligno-cellulosic biomass before fiber shives reduction when using the same amount and composition of the solvent measured 10 minutes after the solvent has been added to the thermally pre-treated ligno-cellulosic biomass before fiber shives reduction and under the same mixing condition when both torque measurements are at 25° C. Preferably the torque of the thermally treated ligno-cellulosic biomass after fiber shives reduction should be at least less than 50% of the torque of the thermally treated ligno-cellulosic biomass before fiber shives reduction, with at least less than 40% even more preferred, with at least less than 30% even more preferred.

It is also preferable that the solvent creating the slurry is not pure recycled process water as offered in WO 2011/044292 and WO 2011/044282, but to use liquid containing solubles and possibly insolubles from a hydrolysis reactor or alternatively use materials derived from the stillage after the hydrolyzed material has been fermented. In another embodiment, the solvent comprises liquids produced during the thermal treatment, said liquids comprising monomeric and oligomeric sugars which have been solubilized as an effect of the thermal treatment. While the addition point in WO 2011/044292 and WO 2011/044282 is at the end of a compounder, the liquid comprising the hydrolysis products of a similarly, if not same, ligno-cellulosic biomass, also considered a solvent in this specification is used to slurry the thermally treated ligno-cellulosic biomass after fiber shives reduction.

The thermally treated ligno-cellulosic biomass, either before and after fiber shives reduction, comprises glucans, xylans and lignin. As the thermal treatment is preferably conducted so as to avoid the removal of all or great amount of the lignin of the starting ligno-cellulosic biomass feedstock, the percent lignin content of the thermally pretreated ligno-cellulosic biomass is greater than 15% by weight on a dry basis. Depending on the feedstock selection and the specific thermal pretreatment, the percent lignin content of the thermally pretreated ligno-cellulosic biomass may be greater than 20%, preferably greater than 25%, more preferably greater than 30%, even more preferably greater than 40%, and most preferably greater than 50%.

The thermally treated ligno-cellulosic biomass, either before and after fiber shive reduction may be further characterized by the ratio of the amount of glucans of the thermally treated ligno-cellulosic biomass to the amount of lignin of the thermally treated ligno-cellulosic biomass, which may be greater than a value selected from the group consisting of 1.5, 1.8, 2.0, 2.2, and 2.5.

Figure 9:
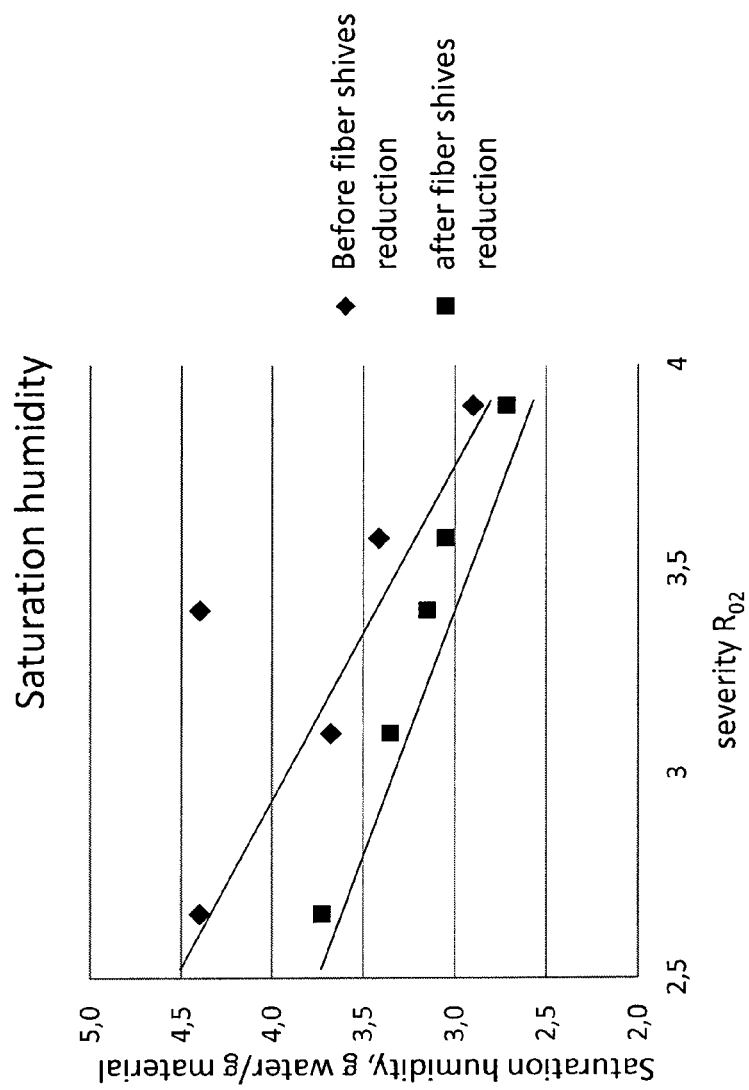
FIG. 9 plots the saturation humidity of thermally treated ligno-cellulosic biomass before and after fiber shives reduction at different severity factors of thermal treatment.

The process can be further characterized, as demonstrated in FIG. 9, by the saturation humidity of the thermally treated ligno-cellulosic biomass after fiber shives reduction and the thermally treated ligno-cellulosic biomass before fiber shives reduction because the saturation humidity of the thermally treated ligno-cellulosic biomass after fiber shives reduction is less than the saturation humidity of thermally treated ligno-cellulosic biomass.

It can be said that thermally treated ligno-cellulosic biomass after fiber shives reduction has a first saturation humidity, and the thermally treated ligno-cellulosic biomass before fiber shives reduction has a second saturation humidity, and the first saturation humidity is less than the second saturation humidity.

In fact, when compared to each other the saturation humidity of the thermally treated ligno-cellulosic biomass after fiber shives reduction is less than a value selected from the group consisting of 20%, 30%, 40%, 50%, 60%, 70% and 80% of the thermally treated ligno-cellulosic biomass before fiber shives reduction.

In terms of output characterization, the saturation humidity of the thermally treated ligno-cellulosic biomass after fiber shives reduction is preferably less than a value selected from the group consisting of 5.5, 5.0, 4.5, 4.0, 3.5, 3.0, 2.5, 2.0, 1.5, and 1.0 g/g expressed as gram of water per gram of thermally treated ligno-cellulosic biomass after fiber shives reduction on a dry basis.

In terms of feedstock selection it is preferable that the saturation humidity of the thermally treated ligno-cellulosic biomass before fiber shives reduction is less than a value selected from the group consisting of 6.0, 5.5, 5.0, 4.5, 4.0, 3.5, 3.0, and 2.5 g/g, expressed as gram of water per gram of thermally treated ligno-cellulosic biomass ligno-cellulosic biomass on a dry basis.

The thermally treated ligno-cellulosic biomass preferably has a dry matter content of at least 20% by weight of the total content of the thermally treated ligno-cellulosic biomass. With the dry matter content of the thermally treated ligno-cellulosic biomass preferably in the range of at least a value selected from the group consisting of 25%, 30%, 35%, and 40% by weight of the total content of the thermally treated ligno-cellulosic biomass to less than 80% by weight of the total content of the thermally treated ligno-cellulosic biomass.

Xylose recovery is the percent ratio between the total amount of xylans in the thermally treated ligno-cellulosic biomass before fiber shives reduction (as xylose equivalents calculated including insoluble xylans, xylo-oligomers, xilobiose and xylose present in both the solid and liquid of the ligno-cellulosic biomass) and the total amount of xylans (converted in xylose equivalents) present in the raw material before the thermal treatment.

The complementary to 100% of the xylose recovery represents therefore the total amount of xylans degradation products as an effect of the thermal treatment.

In the case when the fiber shives reduction converts fiber shives to fines or fibres, the amount of xylose equivalents in the final composition after fiber shives reduction is the same as the amount of xylose equivalents in the thermally treated material before fiber shives reduction.

In terms of xylose recovery, the thermally treated ligno-cellulosic biomass before fiber shives reduction may preferably have a xylose recovery greater than a value selected from the group consisting of 85%, 90%, 92%, 95%, and 98%.

Glucose recovery is the percent ratio between the total amount of glucans in the thermally treated ligno-cellulosic biomass before fiber shives reduction (as glucose equivalents calculated including insoluble glucans, gluco-oligomers, cellobiose and glucose present in both the solid and liquid of the ligno-cellulosic biomass) and the total amount of glucans (converted in glucose equivalents) present in the raw material before the thermal treatment. The complementary to 100% of the glucose recovery represents therefore the total amount of glucans degradation products as an effect of the thermal treatment.

In terms of glucose recovery, the thermally treated ligno-cellulosic biomass before fiber shives reduction preferably has a glucose recovery greater than a value selected from the group consisting of 90%, 92%, 95%, and 98%. The glucans accessibility of the thermally treated ligno-cellulosic biomass before fiber shives reduction is preferably greater than a value selected from the group consisting of 80%, 85%, 88%, 90%, 92%, 95%, and 98% or the glucans accessibility can be lower than a value selected from the group consisting of 75%, 78%, 80%, 82%, 85%, 88% and 91%.

Like xylose, in the case when the fiber shives reduction converts fiber shives to fines or fibres, the amount of glucose equivalents in the final composition after fiber shives reduction is the same as the amount of glucose equivalents in the thermally treated material before fiber shives reduction.

In terms of glucans accessibility, the thermally treated ligno-cellulosic biomass after fiber shives reduction has a first glucans accessibility and the thermally treated ligno-cellulosic biomass before fiber shives reduction has a second glucans accessibility and the first glucans accessibility is greater than the second glucans accessibility.

As the experiments in this specification were done without the addition of acids or bases, it can be said that the thermally treated ligno-cellulosic biomass may preferably be free of added ionic species such as acids or bases, which are species added to the thermally treated ligno-cellulosic biomass after harvesting, i.e. not part of its natural composition. Thus the thermally treated ligno-cellulosic biomass is free of an added acid and/or added base. It is preferred then that if there any ionic groups that the amount and type of ionic groups present in the ligno-cellulosic feedstock are the amounts and types of the respective ionic groups that are not derived from the group consisting of mineral acids, organic acids and organic bases.

The same is true of the process itself of thermal treatment and mechanical treatment as these steps can be conducted in the absence of an added acid and/or added base.

In particular, preferably the thermally treated ligno-cellulosic biomass does not contain sulfur. In the case that sulfur is already present in the ligno-cellulosic biomass feedstock, the percent amount of sulfur by weight in the thermally pretreated ligno-cellulosic biomass on a dry basis is preferably less than a value selected from the group consisting of 4%, 3%, 2, and 1%.

The thermal treatment preferably have a severity ($R_O$) lower than a value selected from the group consisting of 4.0, 3.75, 3.5, 3.25, 3.0, 2.75 and 2.5. The preferred thermal treatment will also comprise a steam explosion step.

In a preferred embodiment, the thermal treatment is conducted at low severity factor, so as to enhance the fiber shives reduction effects in the thermally treated ligno-cellulosic material after fiber shives reduction with respect to the thermally treated ligno-cellulosic biomass before fiber shives reduction. Moreover, the low severity thermal treatment will be more convenient, as it requires less thermal energy. As a consequence the low severity thermally treated ligno-cellulosic biomass after fiber shives reduction will have some peculiar properties.

It is known in the art that a severe thermal treatment has a more remarkable effect on xylans, in terms of solubilization and/or degradation, than on glucans. Thereby, the low severity thermally treated ligno-cellulosic biomass will contain more xylans, with respect to glucans, than a high severity thermally treated ligno-cellulosic biomass, as evident in FIG. 3. This is evident in the graph of FIG. 3. The fiber shives reduction step is conducted substantially to not change the chemical composition of the thermally treated ligno-cellulosic biomass, thereby the thermally treated ligno-cellulosic biomass, either before and after fiber shives reduction, may be characterized by having a percent ratio of the amount of xylans to the amount of glucans which is greater than 5%, more preferably greater than 10%, even more preferably greater than 15%, even more preferably greater than 20%, even yet more preferably greater than 25%, and most preferably greater than 30%. On the other hand, less xylans and glucans degradation products, such as furfural and HMF, will be generated in the thermal treatment.

Low Viscosity Slurry

The formation of a slurry requires the dispersion of the thermally treated ligno-cellulosic biomass in a liquid carrier, wherein the dispersion may occur before, during or after the fiber shives reduction step.

In an embodiment, the carrier liquid is added to the thermally treated ligno-cellulosic biomass after fiber shives reduction.

In another embodiment, is the thermally treated ligno-cellulosic biomass after fiber shives reduction to be added to the carrier liquid.

In another embodiment, is the thermally treated ligno-cellulosic biomass before or during fiber shives reduction to be added to the carrier liquid, and then subjected to fiber shives reduction, for instance by means of a disk refiner or an apparatus to remove shives.

In yet another embodiment, the carrier liquid is added to the thermally treated ligno-cellulosic biomass before or during fiber shives reduction.

Mixing may be applied to promote the dispersion of the treated biomass in the liquid carrier.

In preferred embodiment, the treated biomass is inserted in a vessel and a carrier liquid comprised of water is added to reach a desired dry matter content by weight in the mixture. Liquid may be added, partly or in its entirety, before the insertion into the vessel. Added liquid may be added before or during mixing. Added liquid is preferably added in a continuous way. In one embodiment, the final dry matter in the mixture is 15% or greater and described in further detail below.

In one embodiment, the added liquid carrier comprises water. The added liquid carrier may comprise liquids produced from the thermal treatment of the ligno-cellulosic biomass feedstock, wherein said liquids eventually comprises also undissolved particles of the feedstock. In one embodiment, the added carrier liquid may also comprise dissolved sugars from the thermally treated biomass before or after fiber shives reduction. In another embodiment, the carrier liquid may also comprise soluble species obtainable from either a previously liquefied slurry of the treated ligno-cellulosic biomass after fiber shives reduction or the hydrolysis of the treated ligno-cellulosic biomass after fiber shives reduction. The carrier liquid may or may not contain a hydrolysis catalyst such as an enzyme which hydrolyses the cellulose into glucose In various embodiment, additives may be present in the carrier liquid. Preferably, low shear mixing condition are applied to the mixture, for instance by means of a Rushton impeller. A person skilled in the art knows how to properly apply a low shear to a mixture, by selecting setup and mixing parameters.

As stated previously, the inventors surprisingly discovered that once the carrier liquid contacts the thermally treated ligno-cellulosic biomass after fiber shives reduction, the dispersion of the thermally treated ligno-cellulosic biomass into the carrier liquid proceeds quickly. This is immediately seen by comparing the torque applied to a stirrer disposed in the produced slurry, described as the applied torque, with the applied torque of thermally ligno-cellulosic biomass which has not been subjected to fiber shives reduction, which has also been combined with the carrier liquid, at the same dry weight percent.

Catalytic Conversion to Polyols

The described process comprises a process for generating at least one polyol from the described low viscosity mechanically thermally treated ligno-cellulosic biomass slurry, which may be referred to as the slurry.

In an embodiment, the catalytical conversion is operated in batch mode.

In a preferred embodiment, the process involves continuous catalytic conversion of a flowing stream of the slurry to ethylene glycol or propylene glycol with high yield and high selectivity. Polyol is separated and recovered from the reaction zone effluent. Unreacted hydrogen, water, and at least one co-product are separated from the reaction zone effluent and recycled to the reaction zone, a catalyst system and a process for generating at least one polyol from the slurry comprising at least one saccharide.

In an embodiment, the catalyst system comprises an unsupported component comprising a compound selected from the group consisting of a tungsten compound, a molybdenum compound, and any combination thereof, and a supported component comprising an active metal component selected from the group consisting of Pt, Pd, Ru, Rh, Ni, Ir, and combinations thereof on a solid catalyst support. Examples of suitable solid catalyst supports include carbon, $Al_2O_3$, $ZrO_2$, $SiO_2$, MgO, $Ce_xZrO_y$, $TiO_2$, SiC, silica alumina, zeolites, clays and combinations thereof In another embodiment, the catalyst system comprises a metal component selected from the group consisting of IUPAC Groups 4, 5 and 6 of the Periodic Table, the metal component having an oxidation state greater than or equal to 2+ wherein the metal component is in a form other than a carbide, nitride or phosphide, and a hydrogenation component selected from the group consisting of IUPAC Groups 8, 9, and 10, of the Periodic Table.

The process involves contacting, hydrogen, water, and the slurry, with the catalyst system at reaction conditions to generate an effluent comprising at least one polyol, and recovering the polyol from the effluent.

As described above, the slurry comprises at least cellulose. Economic conversion of cellulose to useful products can be a sustainable process that reduces fossil energy consumption and does not directly compete with the human food supply. Cellulose is a large renewable resource having a variety of attractive sources, such as residue from agricultural production or waste from forestry or forest products. Since cellulose cannot be digested by humans, using cellulose as a feedstock does not take from our food supply. Furthermore, the slurry can be a low cost material which is converted herein to high value products like polyols such as ethylene glycol and propylene glycol.

As described above, the slurry may be derived from sources such as biomass, pulp derived from biomass, waste material, and recycled material. Examples include short rotation forestry, industrial wood waste, forest residue, agricultural residue, energy crops, industrial wastewater, municipal wastewater, paper, cardboard, fabrics and combinations thereof. Multiple materials may be used as co-feedstocks.

Unlike batch system operations, in a continuous process, the slurry is continually being introduced into the reaction zone as a flowing stream and a product comprising a polyol is being continuously withdrawn. Materials must be capable of being transported from a source into the reaction zone, and products must be capable of being transported from the reaction zone. Depending upon the mode of operation, residual solids, if any, may be capable of being removed from the reaction zone.

A challenge in processing a ligno-cellulosic containing feedstock in a pressurized hydrogen environment is that the feedstock is typically a solid. However, the presently described slurry, which exhibits low viscosity, minimizes, at the least, this known problem.

Another challenge in processing a cellulose-containing feedstock, such as the described slurry, is that the cellulose is thermally sensitive. Exposure to excessive heating prior to contacting with the catalyst system may result in undesired thermal reactions of the cellulose such as charring of the cellulose. In one embodiment of the invention, the slurry comprising cellulose is provided to the reaction zone containing the catalyst system in a separate input stream from the primary hydrogen stream. In this embodiment, the reaction zone has at least two input streams. The first input stream comprises at least the slurry comprising cellulose, and the second input stream comprises at least hydrogen. Water may be present in the first input stream, the second input stream or in both input streams. Some hydrogen may also be present in the first input stream with the slurry comprising cellulose. By separating the slurry comprising cellulose and the hydrogen into two independent input streams, the hydrogen stream may be heated in excess of the reaction temperature without also heating the slurry comprising cellulose to reaction temperature or above. The temperature of first input stream comprising at least the slurry comprising cellulose may be controlled not to exceed the temperature of unwanted thermal side reactions. For example, the temperature of first input stream comprising at least the slurry comprising cellulose may be controlled not to exceed the decomposition temperature of the cellulose or the charring temperature of the cellulose. The first input stream, the second input stream, or both may be pressurized to reaction pressure before being introduced to the reaction zone.

The slurry comprising cellulose is continuously introduced to a catalytic reaction zone as a flowing stream. Water and hydrogen, both reactants, are introduced to the reaction zone. As discussed above and depending upon the specific embodiment, at least a portion of the hydrogen may be introduced separately and independent from the slurry comprising cellulose, or any combination of reactants, including slurry comprising cellulose, may be combined and introduced to the reaction zone together. Because of the mixed phases likely to be present in the reaction zone, specific types of systems are preferred. For example, suitable systems include ebullating catalyst bed systems, immobilized catalyst reaction systems having catalyst channels, augured reaction systems, fluidized bed reactor systems, mechanically mixed reaction systems or slurry reactor systems, also known as a three phase bubble column reactor systems.

Furthermore, metallurgy of the reaction zone is selected to be compatible with the reactants and the desired products within the range of operating conditions. Examples of suitable metallurgy for the reaction zone include titanium, zirconium, stainless steel, carbon steel having hydrogen embrittlement resistant coating, carbon steel having corrosion resistant coating. In one embodiment, the metallurgy of the reaction zone includes zirconium clad carbon steel.

Within the reaction zone and at operating conditions, the reactants proceed through catalytic conversion reactions to produce at least one polyol. Desired polyols include ethylene glycol and propylene glycol. At least one co-products is also be produced and may be a compound such as alcohols, organic acids, aldehydes, monosaccharides, polysaccharides, phenolic compounds, hydrocarbons, glycerol, depolymerized lignin, carbohydrates, and proteins. More than one co-product may be produced. Some of the co-products may have value and may be recovered in addition to the product polyols. Co-products may also be reaction intermediates which may be separated from the reaction zone effluent and recycled to the reaction zone. Unreacted hydrogen, water, and cellulose may also be present in the reaction zone effluent along with co-products. Unreacted hydrogen, water, and cellulose may be separated and recycled to the reaction zone. The reaction zone of the process may be operated at conditions sufficient to maintain at least a portion of the water in the reaction mixture in the liquid phase.

The reactions are catalytic reactions and the reaction zone comprises at least one catalyst system. The catalyst system for conversion of saccharide to at least one polyol comprises an unsupported component comprising a compound selected from the group consisting of a tungsten compound, a molybdenum compound, and any combination thereof; and a supported component comprising an active metal component selected from the group consisting of Pt, Pd, Ru, Rh, Ni, Ir, and combinations thereof on a solid catalyst support. Multiple active metals may be present on the solid catalyst support. Examples of suitable unsupported components include tungstic acid, molybedic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, and combinations thereof. One or more unsupported catalyst components may be used with one or more supported catalyst components. The catalyst system may also be considered a multi-component catalyst, and the terms are used herein interchangeably.

The supported catalyst component of the catalyst system requires a solid catalyst support. The support may be in the shape of a powder, or specific shapes such as spheres, extrudates, pills, pellets, tablets, irregularly shaped particles, monolithic structures, catalytically coated tubes, or catalytically coated heat exchanger surfaces. The active metal may be incorporated onto the catalytic support in any suitable manner known in the art, such as by coprecipitation, coextrusion with the support, or impregnation. The active metal may be in the reduced form. Refractory oxide catalyst supports and others may be used. Examples of the refractory inorganic oxide supports include but are not limited to silica, aluminas, silica-alumina, titania, zirconia, magnesia, clays, zeolites, molecular sieves, etc. It should be pointed out that silica-alumina is not a mixture of silica and alumina but means an acidic and amorphous material that has been cogelled or coprecipitated. Carbon and activated carbon may also be employed as supports. Specific suitable supports include carbon, activated carbon, $Al_2O_3$, $ZrO_2$, $SiO_2$, MgO, $Ce_xZrO_y$, $TiO_2$, SiC, silica alumina, zeolites, clays and combinations thereof. Of course, combinations of materials can be used as the support. The active metal may comprise from about 0.05 to about 30 mass % of the supported catalyst component. In another embodiment of the invention, the active metal may comprise from about 0.3 to about 15 mass % of the supported catalyst component, and in another embodiment of the invention the active metal may comprise from about 0.5 to about 7 mass % of the supported catalyst component.

As measured on an elemental basis, the relative amount of unsupported catalyst component to supported catalyst component may range from about 1:100 to about 100:1 as measured by ICP or other common wet chemical analysis methods, on an elemental basis. In another embodiment, the relative amount of unsupported catalyst component to supported catalyst component may range from about 1:20 to about 50:1, on an elemental basis, and in still another embodiment, the relative amount of supported catalyst component to unsupported catalyst component may range from about 1:10 to about 10:1, on an elemental basis.

The amount of the catalyst system used in the process may range from about 0.005 to about 0.4 mass % of the slurry comprising saccharide, with the catalyst system measured on an elemental basis. In other embodiment, the amount of the catalyst system used in the process may range from about 0.01 to about 0.25 mass % of the slurry comprising saccharide, with the catalyst system measured on an elemental basis. In still other embodiment, the amount of the catalyst system used in the process may range from about 0.02 to about 0.15 mass % of the slurry comprising saccharide, with the catalyst system measured on an elemental basis. The reactions occurring are multistep reactions and different amounts of the catalyst system, or relative amounts of the components of the catalyst system, can be used to control the rates of the different reactions. Individual applications may have differing requirements as to the amounts of the catalyst system, or relative amounts of the components of the catalyst system used.

In one embodiment of the invention, the unsupported catalyst component may be a solid that is soluble in the reaction mixture, or at least partially soluble in the reaction mixture which includes at least water and the slurry at reaction conditions. An effective amount of the unsupported catalyst should be soluble in the reaction mixture. Different applications and different unsupported catalyst components will result in differing effective amounts of unsupported catalyst component needed to be in solution in the reaction mixture. In another embodiment of the invention, the unsupported catalyst component is a liquid which is miscible or at least partially miscible with the reaction mixture. As with the solid unsupported catalyst component, an effective amount of the liquid unsupported catalyst should be miscible in the reaction mixture. Again, different applications and different unsupported catalyst components will result in differing effective amounts of unsupported catalyst component needed to be miscible in the reaction mixture. Typically, the amount of unsupported catalyst component miscible in water is in the range of about 1 to about 100%, on an elemental basis, in another embodiment, from about 10 to about 100%, on an elemental basis, and in still another embodiment, from about 20 to about 100%, on an elemental basis.

The multicomponent catalyst of the present invention may provide several advantages over a more traditional single component catalyst. For example, in some embodiments, the manufacture costs of the catalyst may be reduced since fewer active components need to be incorporated onto a solid catalyst support. Operational costs may be reduced since it is envisioned that less catalyst make-up will be required and more selective processing steps can be used for recovery and recycle of catalyst. Other advantages include improved catalyst stability which leads to lower catalyst consumption and lower cost per unit of polyol product, and the potential for improved selectivity to ethylene glycol and propylene glycol with reduced production of co-boiling impurities such as butane diols.

In some embodiments, all or a portion of the catalyst system may reside within the reaction zone, and in other embodiments, the catalyst may continuously or intermittently pass through the reaction zone. Suitable systems include ebullating catalyst bed systems, immobilized catalyst reaction systems having catalyst channels, augured reaction systems, fluidized bed reactor systems, mechanically mixed reaction systems and slurry reactor systems, also known as a three phase bubble column reactor systems.

In one embodiment of the invention, the catalytic reaction zone employs a slurry reactor. Slurry reactor systems are known in the art and an example of a slurry reactor system is described in U.S. Pat. No. 5,616,304.

The catalyst system may be mixed with the slurry comprising cellulose and conducted to the slurry reactor. The reactions occur within the slurry reactor and the catalyst is transported with the effluent stream out of the reactor. The slurry reactor system may be operated at temperatures from about 100° C. to about 350° C. and the hydrogen pressure may be greater than about 150 psig. In one embodiment, the temperature in the slurry reactor system may range from about 15.0° C. to about 350° C., in another embodiment the temperature in the slurry reactor system may range from about 200° C. to about 280° C. The slurry may be continuously contacted with the catalyst system in a slurry reactor system operated at a water to slurry comprising cellulose weight ratio ranging from about 1 to about 100, a catalyst to slurry comprising cellulose weight ratio of greater than about 0.005, a pH of less than about 10 and a residence time of greater than 5 minutes. In another embodiment, the water to slurry comprising cellulose weight ratio ranges from about 1 to about 20 and the catalyst system to slurry comprising cellulose weight ratio is greater than about 0.01 with the catalyst system measured on an elemental basis. In yet another embodiment, the water to slurry comprising cellulose weight ratio ranges from about 1 to about 5 and the catalyst to slurry comprising cellulose weight ratio is greater than about 0.1 with the catalyst system measured on an elemental basis.

In another embodiment, the catalytic reaction zone employs an ebullating bed reactor. Ebullating bed reactor systems are known in the art and an example of an ebullating bed reactor system is described in U.S. Pat. No. 6,436,279.

The effluent stream from the reaction zone contains at least the product polyol(s) and unreacted water, hydrogen, and at least one co-product such as alcohols, organic acids, aldehydes, monosaccharides, polysaccharides, phenolic compounds, hydrocarbons, glycerol, depolymerized lignin, carbohydrates, and proteins. Unreacted cellulose may also be present in the reaction zone effluent stream. At least the water, hydrogen, and one co-product are separated from the reaction zone effluent stream and recycled to the reaction zone. Unreacted cellulose may also be separated from the reaction zone effluent stream and recycled to the reaction zone.

In one embodiment, the hydrogen is separated from the effluent stream before the water is separated from the effluent stream. The separated hydrogen may be recycled to one or more of a number of different locations within the process depending upon the specific embodiment employed. For example, the separated hydrogen maybe recycled to a reactor in the reaction zone. The recycled hydrogen may be combined with fresh hydrogen or make-up hydrogen before being introduced into a reactor of the reaction zone, or recycled hydrogen may be introduced to a reactor in the reaction zone independently of fresh hydrogen or make-up hydrogen. The separated hydrogen may be pressurized to the pressure of the reaction zone, and heated to or above the temperature of the reaction zone. The separated hydrogen may be purified before recycling. A gas-liquid separator may be used to separate the hydrogen from the effluent stream.

Similarly, the water may be recycled to one or more of a number of different locations within the process depending upon the specific embodiment employed. For example, the separated water may be recycled to combine with the slurry comprising cellulose. The separated water may be added to an optional pretreatment operation, or may be added to the reaction zone. The water may be purified before being recycled.

Furthermore, the reaction zone may comprise a mixing zone upstream of a reactor. When a mixing zone is employed, the separated hydrogen may be recycled to the reactor while the separated water may be recycled to the mixing zone.

In a product recovery zone, at least the polyols are separated from the effluent stream. In one embodiment, the co-products are also separated from the effluent stream in the product recovery zone. Multiple separated stream may be produced by the product recovery zone; ethylene glycol may be separated into an ethylene glycol stream, propylene glycol maybe separated into a propylene glycol stream, co-products having a molecular weight lower than ethylene glycol, such as alcohols, may be separated into a low molecular weight co-product stream, co-products having a molecular weight higher than propylene glycol, such as glycerol, may be separated into a high molecular weight co-product stream, fuel gas may be separated into a fuel gas stream, and non-volatile residues may be separated into a non-volatile residue stream. Additional co-product streams may be separated so that classes or individual co-products are separated. One or more of the co-products streams may be recycled to the reaction zone. In the embodiment where the reaction zone comprises a mixing zone upstream of a reactor, the separated at least one co-product may be recycled to the reactor, the mixing zone, or both. Depending upon the catalyst selected and the catalytic reaction system used, the product recovery zone may also separate catalyst from the effluent stream. The product polyol stream(s) may be purified in a product purification zone to generate high purity polyol.

Depending on the catalytic reaction system used, the effluent stream may also contain solid catalyst particles. In some embodiments it may be advantageous to remove the solid catalyst particles from the effluent stream, either before or after the desired products or co-products are recovered. Catalyst particles may be removed from the effluent stream using one or more techniques such as direct filtration, settling followed by filtration, hydrocyclone, fractionation, centrifugation, the use of flocculants, precipitation, extraction, evaporation, or combinations thereof. In one embodiment, the catalyst particles are separated from the effluent stream after the hydrogen is separated from the effluent stream and before the water is separated from the effluent stream. In another embodiment, separated catalyst particles may be recycled to the reaction zone. In yet another embodiment, the separated catalyst particles may be reactivated before being recycled to the reaction zone. In the embodiment where the reaction zone comprises a mixing zone upstream of a reactor, the separated at least one co-product may be recycled to the reactor, the mixing zone, or both.

Figure 13:
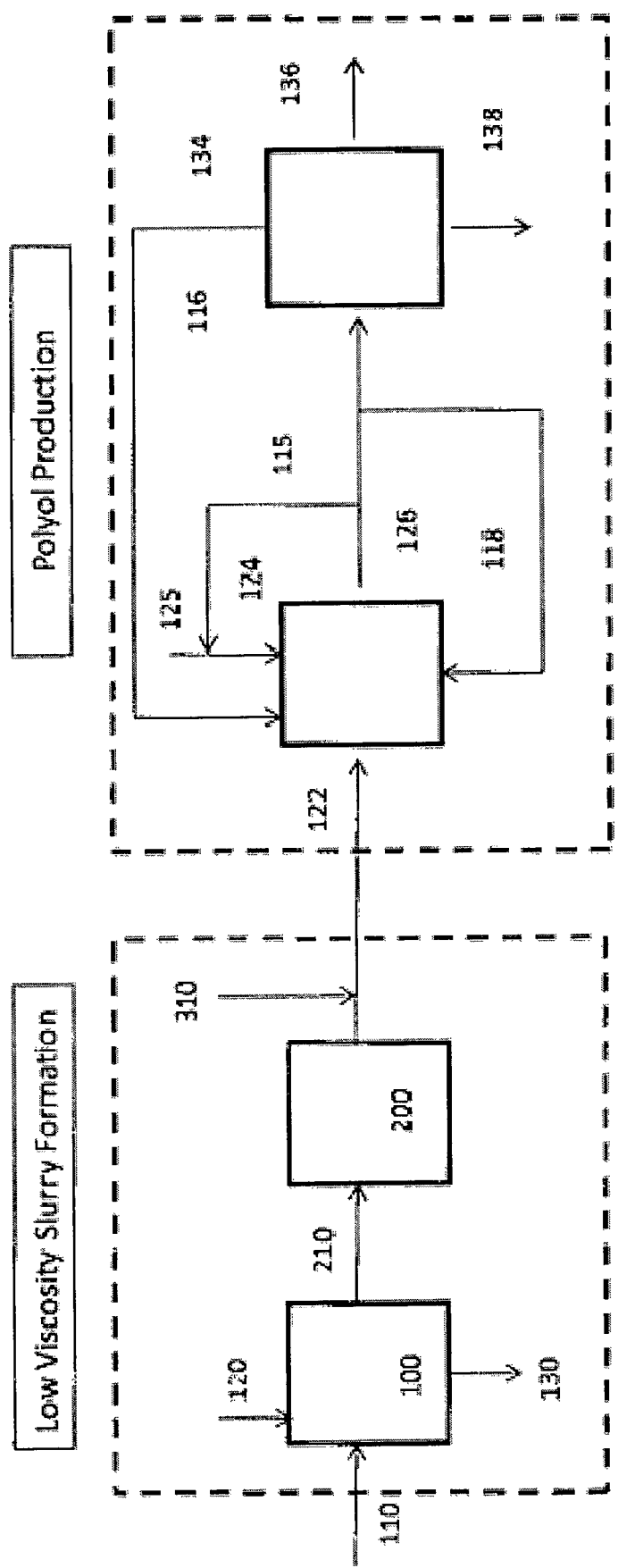
FIG. 13 shows a schematic of the formation of a low viscosity ligno-cellulosic biomass slurry and the subsequent formation of polyols, according to one embodiment.

Turning to FIG. 13, preparation of the low viscosity slurry, as described above, is performed in zone 100 (thermal treatment) and 200 (mechanical treatment), and combined with the carrier liquid 310 to form the slurry. Catalyst, water, and slurry comprising cellulose is conducted via stream 122 to reaction zone 124. The mixture in stream 122 has, for example, a water to slurry comprising cellulose weight ratio of about 5 and a catalyst to slurry comprising cellulose weight ratio of about 0.05. At least hydrogen is conducted via stream 125 to reaction zone 124. Reaction zone 124 is operated at, for example, a temperature of about 250° C. a hydrogen pressure of about 1200 psig, a pH of about 7 and a residence time of about 8 minutes. Prior to introduction into reaction zone 124, the catalyst, water, and slurry comprising cellulose in stream 122 and the hydrogen in stream 125 are brought to a pressure of about 1800 psig to be at about the same pressure as reaction zone 124. However, only stream 125 comprising at least hydrogen, while upstream of zone 124, is raised to at least 250° C. to be at about the temperature of reaction zone 124. The mixture in stream 122 which contains at least the cellulose is temperature controlled to remain at a temperature lower than the decomposition or charring temperature of the cellulose. In reaction zone 124, the cellulose is catalytically converted into at least ethylene glycol or polyethylene glycol. Reaction zone effluent 126 contains at least the product ethylene glycol or propylene glycol, hydrogen, water, and at least one co-product such as alcohols, organic acids, aldehydes, monosaccharides, polysaccharides, phenolic compounds, hydrocarbons, glycerol, depolymerized lignin, carbohydrates, and proteins. Hydrogen is separated from reaction zone effluent in line 115 and recycled to reaction zone 124. The separated hydrogen in line 115 may be combined with hydrogen stream 125 as shown. Water is separated from reaction zone effluent in line 118 and recycled to reaction zone 124. The remaining portion of reaction zone effluent 126 is conducted to product recovery zone 134 where the desired glycol products are separated and recovered in steam 136. At least one co-product is separated into co-product stream 116 and recycled to reaction zone 124. Remaining components of reaction zone effluent 126 are removed from product recovery zone 134 in stream 138.

In various embodiments, the reaction zone contains mixing zone and reactor. The slurry is conducted to mixing zone of reaction zone and combined with water and catalyst. Mixed stream from mixing zone has, for example, a water to slurry comprising cellulose weight ratio of about 5 and a catalyst to slurry comprising cellulose weight ratio of about 0.05. At least hydrogen is conducted to reactor of reaction zone. Some hydrogen may be combined with either stream prior to reactor. Reactor is operated at, for example, a temperature of about 250° C., a hydrogen pressure of about 1200 psig, a pH of about 7 and a residence time of about 8 minutes. Prior to introduction into reactor, the catalyst, water, and slurry comprising cellulose in one stream and the hydrogen in another stream are brought to a pressure of about 1800 psig to be at about the same temperature as reactor. However, only the stream comprising at least hydrogen, while upstream of reactor, is raised to, for example, at least 250° C. to be about the temperature of reactor. The mixture in the stream which contains at least the cellulose is temperature controlled to remain at a temperature lower than the decomposition or charring temperature of the cellulose. In reactor, the cellulose is catalytically converted into at least ethylene glycol or polyethylene glycol.

Reactor effluent contains at least the product ethylene glycol or propylene glycol, hydrogen, water, at least one co-product and catalyst. The at least one co-product may be alcohols, organic acids, aldehydes, monosaccharides, polysaccharides, phenolic compounds, hydrocarbons, glycerol, depolymerized lignin, carbohydrates, and proteins. Reactor effluent is conducted to a hydrogen separation zone 2 where at least a portion of the hydrogen is removed and recycled to reactor through combining with hydrogen stream or directly to reactor. The hydrogen depleted reactor effluent is conducted to a water separation zone where at least a portion of the water is separated and recycled to mixing zone by combining with water stream or directly to mixing zone.

Hydrogen and water depleted reactor effluent is conducted to optional catalyst recovery zone where the catalyst is separated and removed. Catalyst may optionally be recycled to combine or directly to mixing zone. The catalyst-depleted reactor effluent is conducted to product recovery zone where the desired glycol products are separated and recovered in steam. At least one co-product is separated and recycled to mixing zone. Remaining components of catalyst-depleted reactor effluent are removed from product recovery zone.

These above embodiments are not designed to limit the specification or claims, as there are many configurations available to one of ordinary skill, which include a series of continuous vessels, or semi batch reactors or in combination with or without plug flow reactors.

Feedstock Selection

Because the feedstock may use naturally occurring ligno-cellulosic biomass, the stream will have relatively young carbon materials. The following, taken from ASTM D 6866-04 describes the contemporary carbon, which is that found in bio-based hydrocarbons, as opposed to hydrocarbons derived from oil wells, which was derived from biomass thousands of years ago. "[A] direct indication of the relative contribution of fossil carbon and living biospheric carbon can be as expressed as the fraction (or percentage) of contemporary carbon, symbol $f_C$. This is derived from $f_M$ through the use of the observed input function for atmospheric $^{14}C$ over recent decades, representing the combined effects of fossil dilution of the $^{14}C$ (minor) and nuclear testing enhancement (major). The relation between $f_C$ and $f_M$ is necessarily a function of time. By 1985, when the particulate sampling discussed in the cited reference [of ASTM D 6866-04, the teachings of which are incorporated by reference in their entirety] the $f_M$ ratio had decreased to ca. 1.2."

Fossil carbon is carbon that contains essentially no radiocarbon because its age is very much greater than the 5730 year half life of $^{14}C$. Modern carbon is explicitly 0.95 times the specific activity of SRM 4990b (the original oxalic acid radiocarbon standard), normalized to $\delta^{13}C=-19\%$. Functionally, the faction of modern carbon=(1/0.95) where the unit 1 is defined as the concentration of $^{14}C$ contemporaneous with 1950 [A.D.] wood (that is, pre-atmospheric nuclear testing) and 0.95 are used to correct for the post 1950 [A.D.] bomb $^{14}C$ injection into the atmosphere. As described in the analysis and interpretation section of the test method, a 100% $^{14}C$ indicates an entirely modern carbon source, such as the products derived from this process. Therefore, the percent $^{14}C$ of the product stream from the process will be at least 75%, with 85% more preferred, 95% even preferred and at least 99% even more preferred and at least 100% the most preferred. (The test method notes that the percent $^{14}C$ can be slightly greater than 100% for the reasons set forth in the method). These percentages can also be equated to the amount of contemporary carbon as well.

Therefore the amount of contemporary carbon relative to the total amount of carbon is preferred to be at least 75%, with 85% more preferred, 95% even more preferred and at least 99% even more preferred and at least 100% the most preferred. Correspondingly, each carbon containing compound in the reactor, which includes a plurality of carbon containing conversion products will have an amount of contemporary carbon relative to total amount of carbon is preferred to be at least 75%, with 85% more preferred, 95% even preferred and at least 99% even more preferred and at least 100% the most preferred.

In general, a natural or naturally occurring ligno-cellulosic biomass can be one feed stock for this process. Ligno-cellulosic materials can be described as follows:

Apart from starch, the three major constituents in plant biomass are cellulose, hemicellulose and lignin, which are commonly referred to by the generic term lignocellulose. Polysaccharide-containing biomasses as a generic term include both starch and ligno-cellulosic biomasses. Therefore, some types of feedstocks can be plant biomass, polysaccharide containing biomass, and ligno-cellulosic biomass.

Polysaccharide-containing biomasses according to the present invention include any material containing polymeric sugars e.g. in the form of starch as well as refined starch, cellulose and hemicellulose.

Relevant types of naturally occurring biomasses for deriving the claimed invention may include biomasses derived from agricultural crops selected from the group consisting of starch containing grains, refined starch; corn stover, bagasse, straw e.g. from rice, wheat, rye, oat, barley, rape, sorghum; softwood e.g. *Pinus sylvestris, Pinus radiate*; hardwood e.g. *Salix* spp. *Eucalyptus* spp.; tubers e.g. beet, potato; cereals from e.g. rice, wheat, rye, oat, barley, rape, sorghum and corn; waste paper, fiber fractions from biogas processing, manure, residues from oil palm processing, municipal solid waste or the like. Although the experiments are limited to a few examples of the enumerated list above, the invention is believed applicable to all because the characterization is primarily to the unique characteristics of the lignin and surface area.

The ligno-cellulosic biomass feedstock used to derive the composition is preferably from the family usually called grasses. The proper name is the family known as Poaceae or Gramineae in the Class Liliopsida (the monocots) of the flowering plants. Plants of this family are usually called grasses, or, to distinguish them from other graminoids, true grasses. Bamboo is also included. There are about 600 genera and some 9,000-10,000 or more species of grasses (Kew Index of World Grass Species).

Poaceae includes the staple food grains and cereal crops grown around the world, lawn and forage grasses, and bamboo. Poaceae generally have hollow stems called culms, which are plugged (solid) at intervals called nodes, the points along the culm at which leaves arise. Grass leaves are usually alternate, distichous (in one plane) or rarely spiral, and parallel-veined. Each leaf is differentiated into a lower sheath which hugs the stem for a distance and a blade with margins usually entire. The leaf blades of many grasses are hardened with silica phytoliths, which helps discourage grazing animals. In some grasses (such as sword grass) this makes the edges of the grass blades sharp enough to cut human skin. A membranous appendage or fringe of hairs, called the ligule, lies at the junction between sheath and blade, preventing water or insects from penetrating into the sheath.

Grass blades grow at the base of the blade and not from elongated stem tips. This low growth point evolved in response to grazing animals and allows grasses to be grazed or mown regularly without severe damage to the plant.

Flowers of Poaceae are characteristically arranged in spikelets, each spikelet having one or more florets (the spikelets are further grouped into panicles or spikes). A spikelet consists of two (or sometimes fewer) bracts at the base, called glumes, followed by one or more florets. A floret consists of the flower surrounded by two bracts called the lemma (the external one) and the palea (the internal). The flowers are usually hermaphroditic (maize, monoecious, is an exception) and pollination is almost always anemophilous. The perianth is reduced to two scales, called lodicules, that expand and contract to spread the lemma and palea; these are generally interpreted to be modified sepals.

The fruit of Poaceae is a caryopsis in which the seed coat is fused to the fruit wall and thus, not separable from it (as in a maize kernel).

There are three general classifications of growth habit present in grasses; bunch-type (also called caespitose), stoloniferous and rhizomatous.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized Kranz leaf anatomy that particularly adapts them to hot climates and an atmosphere low in carbon dioxide.

C3 grasses are referred to as "cool season grasses" while C4 plants are considered "warm season grasses". Grasses may be either annual or perennial. Examples of annual cool season are wheat, rye, annual bluegrass (annual meadowgrass, *Poa annua* and oat). Examples of perennial cool season are orchard grass (cocksfoot, *Dactylis glomerata*), fescue (*Festuca* spp), Kentucky Bluegrass and perennial ryegrass (*Lolium perenne*). Examples of annual warm season are corn, sudangrass and pearl millet. Examples of Perennial Warm Season are big bluestem, indian grass, bermuda grass and switch grass.

One classification of the grass family recognizes twelve subfamilies: These are 1) anomochlooideae, a small lineage of broad-leaved grasses that includes two genera (*Anomochloa, Streptochaeta*); 2) Pharoideae, a small lineage of grasses that includes three genera, including *Pharus* and *Leptaspis;* 3) Puelioideae a small lineage that includes the African genus *Puelia;* 4) Pooideae which includes wheat, barley, oats, brome-grass (Bronnus) and reed-grasses (*Calamagrostis*); 5) Bambusoideae which includes bamboo; 6) Ehrhartoideae, which includes rice, and wild rice; 7) Arundinoideae, which includes the giant reed and common reed; 8) Centothecoideae, a small subfamily of 11 genera that is sometimes included in Panicoideae; 9) Chloridoideae including the lovegrasses (*Eragrostis*, ca. 350 species, including teff), dropseeds (*Sporobolus*, some 160 species), finger millet (*Eleusine coracana* (L.) Gaertn.), and the muhly grasses (*Muhlenbergia*, ca. 175 species); 10) Panicoideae including panic grass, maize, sorghum, sugar cane, most millets, fonio and bluestem grasses; 11) Micrairoideae and 12) Danthoniodieae including pampas grass; with *Poa* which is a genus of about 500 species of grasses, native to the temperate regions of both hemispheres.

Agricultural grasses grown for their edible seeds are called cereals. Three common cereals are rice, wheat and maize (corn). Of all crops, 70% are grasses.

Sugarcane is the major source of sugar production. Grasses are used for construction. Scaffolding made from bamboo is able to withstand typhoon force winds that would break steel scaffolding. Larger bamboos and *Arundo donax* have stout culms that can be used in a manner similar to timber, and grass roots stabilize the sod of sod houses. *Arundo* is used to make reeds for woodwind instruments, and bamboo is used for innumerable implements.

Another naturally occurring ligno-cellulosic biomass feedstock may be woody plants or woods. A woody plant is a plant that uses wood as its structural tissue. These are typically perennial plants whose stems and larger roots are reinforced with wood produced adjacent to the vascular tissues. The main stem, larger branches, and roots of these plants are usually covered by a layer of thickened bark. Woody plants are usually either trees, shrubs, or lianas. Wood is a structural cellular adaptation that allows woody plants to grow from above ground stems year after year, thus making some woody plants the largest and tallest plants.

These plants need a vascular system to move water and nutrients from the roots to the leaves (xylem) and to move sugars from the leaves to the rest of the plant (phloem). There are two kinds of xylem: primary that is formed during primary growth from procambium and secondary xylem that is formed during secondary growth from vascular cambium.

What is usually called "wood" is the secondary xylem of such plants.

The two main groups in which secondary xylem can be found are:

1) conifers (Coniferae): there are some six hundred species of conifers. All species have secondary xylem, which is relatively uniform in structure throughout this group. Many conifers become tall trees: the secondary xylem of such trees is marketed as softwood.
2) angiosperms (Angiospermae): there are some quarter of a million to four hundred thousand species of angiosperms. Within this group secondary xylem has not been found in the monocots (e.g. Poaceae). Many non-monocot angiosperms become trees, and the secondary xylem of these is marketed as hardwood.

The term softwood useful in this process is used to describe wood from trees that belong to gymnosperms. The gymnosperms are plants with naked seeds not enclosed in an ovary. These seed "fruits" are considered more primitive than hardwoods. Softwood trees are usually evergreen, bear cones, and have needles or scale like leaves. They include conifer species e.g. pine, spruces, firs, and cedars. Wood hardness varies among the conifer species.

The term hardwood useful for this process is used to describe wood from trees that belong to the angiosperm family. Angiosperms are plants with ovules enclosed for protection in an ovary. When fertilized, these ovules develop into seeds. The hardwood trees are usually broad-leaved; in temperate and boreal latitudes they are mostly deciduous, but in tropics and subtropics mostly evergreen. These leaves can be either simple (single blades) or they can be compound with leaflets attached to a leaf stem. Although variable in shape all hardwood leaves have a distinct network of fine veins. The hardwood plants include e.g. Aspen, Birch, Cherry, Maple, Oak and Teak.

Therefore a preferred naturally occurring ligno-cellulosic biomass may be selected from the group consisting of the grasses and woods. Another preferred naturally occurring ligno-cellulosic biomass can be selected from the group consisting of the plants belonging to the conifers, angiosperms, Poaceae and families. Another preferred naturally occurring ligno-cellulosic biomass may be that biomass having at least 10% by weight of it dry matter as cellulose, or more preferably at least 5% by weight of its dry matter as cellulose.

The carbohydrate(s) comprising the invention is selected from the group of carbohydrates based upon the glucose, xylose, and mannose monomers and mixtures thereof.

The feedstock comprising lignin can be naturally occurring ligno-cellulosic biomass that has been ground to small particles, or one which has been further processed. One process for creating the feedstock comprising lignin, comprises the following steps.

Preferable Pretreatment

It has been theorized that pretreatment of the feedstock is a solution to the challenge of processing an insoluble solid feedstock comprising lignin or polysaccharides in a pressurized environment. According to US 2011/0312051, sizing, grinding, drying, hot catalytic treatment and combinations thereof are suitable pretreatment of the feedstock to facilitate the continuous transporting of the feedstock. While not presenting any experimental evidence, US 2011/0312051 claims that mild acid hydrolysis of polysaccharides, catalytic hydrogenation of polysaccharides, or enzymatic hydrolysis of polysaccharides are all suitable to create a transportable feedstock. US 2011/0312051 also claims that hot water treatment, steam treatment, thermal treatment, chemical treatment, biological treatment, or catalytic treatment may result in lower molecular weight polysaccharides and depolymerized lignins that are more easily transported as compared to the untreated ones. While this may help transport, there is no disclosure or solution to how to pressurize the solid/liquid slurry resulting from the pre-treatment. In fact, as the inventors have learned the conventional wisdom and conventional systems used for pressuring slurries failed when pre-treated ligno-cellulosic biomass feedstock is used.

In the integrated second generation industrial operations, pre-treatment is often used to ensure that the structure of the ligno-cellulosic content is rendered more accessible to the catalysts, such as enzymes, and at the same time the concentrations of harmful inhibitory by-products such as acetic acid, furfural and hydroxymethyl furfural remain substantially low. There are several strategies to achieve increased accessibility, many of which may yet be invented.

The current pre-treatment strategies imply subjecting the ligno-cellulosic biomass material to temperatures between 110-250° C. for 1-60 min e.g.: Hot water extraction Multistage dilute acid hydrolysis, which removes dissolved material before inhibitory substances are formed
Dilute acid hydrolyses at relatively low severity conditions
Alkaline wet oxidation
Steam explosion.

A preferred pretreatment of a naturally occurring ligno-cellulosic biomass includes a soaking of the naturally occurring ligno-cellulosic biomass feedstock and a steam explosion of at least a part of the soaked naturally occurring ligno-cellulosic biomass feedstock.

The soaking occurs in a substance such as water in either vapor form, steam, or liquid form or liquid and steam together, to produce a product. The product is a soaked biomass containing a first liquid, with the first liquid usually being water in its liquid or vapor form or some mixture.

This soaking can be done by any number of techniques that expose a substance to water, which could be steam or liquid or mixture of steam and water, or, more in general, to water at high temperature and high pressure. The temperature should be in one of the following ranges: 145 to 165° C., 120 to 210° C., 140 to 210° C., 150 to 200° C., 155 to 185° C., 160 to 180° C. Although the time could be lengthy, such as up to but less than 24 hours, or less than 16 hours, or less than 12 hours, or less than 9 hours, or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

If steam is used, it is preferably saturated, but could be superheated. The soaking step can be batch or continuous, with or without stirring. A low temperature soak prior to the high temperature soak can be used. The temperature of the low temperature soak is in the range of 25 to 90° C. Although the time could be lengthy, such as up to but less than 24 hours, or less than 16 hours, or less than 12 hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

Either soaking step could also include the addition of other compounds, e.g. $H_2SO_4$, $NH_3$, in order to achieve higher performance later on in the process. However, it is preferred that acid, base or halogens not be used anywhere in the process or pre-treatment. The feedstock is preferably void of added sulfur, halogens, or nitrogen. The amount of sulfur, if present, in the composition is in the range of 0 to 1% by dry weight of the total composition. Additionally, the amount of total halogens, if present, are in the range of 0 to 1% by dry weight of the total composition. By keeping halogens from the feedstock, there are no halogens in the lignin conversion products.

The product comprising the first liquid is then passed to a separation step where the first liquid is separated from the soaked biomass. The liquid will not completely separate so that at least a portion of the liquid is separated, with preferably as much liquid as possible in an economic time frame. The liquid from this separation step is known as the first liquid stream comprising the first liquid. The first liquid will be the liquid used in the soaking, generally, water and the soluble species of the feedstock. These water soluble species are glucan, xylan, galactan, arabinan, glucolygomers, xyloolygomers, galactolygomers and arabinolygomers. The solid biomass is called the first solid stream as it contains most, if not all, of the solids.

The separation of the liquid can again be done by known techniques and likely some which have yet to be invented. A preferred piece of equipment is a press, as a press will generate a liquid under high pressure.

The first solid stream is then steam exploded to create a steam exploded stream, comprising solids and a second liquid. Steam explosion is a well known technique in the biomass field and any of the systems available today and in the future are believed suitable for this step. The severity of the steam explosion is known in the literature as Ro, and is a function of time and temperature and is expressed as in the Experimental Section.

Experimental
Preparation of Thermally Treated Ligno-Cellulosic Biomass

Wheat straw was used as the ligno-cellulosic biomass feedstock.

Wheat straw was subjected to a thermal treatment composed of a soaking step followed by a steam explosion step according to the following procedure.

Ligno-cellulosic biomass was introduced into a continuous reactor and subjected to a soaking treatment. The soaked mixture was separated into a soaked liquid and a fraction containing the solid soaked raw material by means of a press. The fraction containing the solid soaked raw material was subjected to steam explosion. Steam exploded products were separated into a steam explosion liquid and a steam exploded solid. Steam exploded solid is the exemplary thermally treated ligno-cellulosic biomass before fiber shives reduction used in the present experimental section and they are indicated by the -BSR (Before fiber Shives Reduction) extension following the sample code.

Pretreatment parameters of the ligno-cellulosic biomass are reported in Table 1.

Severity of each thermal treatment step $R_{o1}$ and $R_{o2}$ was calculated according the formula:

$$R_{o1}=\log_{10}(Q_1), \text{ wherein}$$

$$Q_1=t_1\exp((T_1-100)/14.75)$$

$$R_{o2}=\log_{10}(Q_2), \text{ wherein}$$

$$Q_2=t_2\exp((T_2-100)/14.75),$$

wherein time $t_1$ and $t_2$ is measured in minutes and temperature $T_1$ and $T_2$ is measured in Celsius.

The total severity factor $R_0$ was calculated according to the formula:

$$R_0=\log_{10}(Q_1+Q_2)$$

TABLE 1

Process parameters used in the thermal treatment

| Sample | Soaking Temperature (° C.) | Soaking Time (minutes) | Steam explosion Temperature (° C.) | Steam explosion Time (minutes) | $R_{O1}$ | $R_{O2}$ | $R_O$ |
|---|---|---|---|---|---|---|---|
| S01-BSR | 155 | 65 | 180 | 2 | 3.43 | 2.66 | 3.50 |
| S02-BSR | 155 | 65 | 195 | 2 | 3.43 | 3.10 | 3.60 |
| S03-BSR | 155 | 65 | 187 | 8 | 3.43 | 3.46 | 3.75 |
| S04-BSR | 155 | 65 | 195 | 4 | 3.43 | 3.40 | 3.72 |
| S05-BSR | 155 | 65 | 202 | 8 | 3.43 | 3.91 | 4.03 |
| S06-BSR | 155 | 65 | 210 | 16 | 3.43 | 4.44 | 4.48 |
| S07-BSR | 158 | 65 | 201.5 | 4 | 3.52 | 3.59 | 3.86 |
| S08-BSR | 158 | 65 | 202.5 | 2 | 3.52 | 3.32 | 3.73 |

Fiber Shives Reduction of the Thermally Treated Ligno-Cellulosic Biomass

All the thermally treated ligno-cellulosic biomass were subjected to a fiber shives reduction step by means of a counter-rotating twin screw extruder (Welding Engineers Inc., model HTR 30 MM (HTR 30.22.22.22.13.E1), Blue Bell, Pa.), barrel length to screw diameter ratio of 54:1. The machine was fitted to a 25-hp motor, which has a provision to adjust the screw speed from 0 to 500 rpm. The parameters of the profile of the screws are reported in FIG. 1.

The thermally treated ligno-cellulosic biomass was treated at 250 rpm to reduce fiber shives. The thermally treated ligno-cellulosic biomass was inserted in the extruder at a temperature of 25° C. The thermally treated ligno-cellulosic biomass exited the extruder as a solid at about 25° C. The thermally treated ligno-cellulosic biomass was inserted manually in the extruder at an inlet rate of approximately 5 Kg/h on wet basis, at a moisture content of about 60%. Residence time was estimated be to approximately 3 minutes.

The specific energy consumption for fiber shives reducing a Kg of thermally treated ligno-cellulosic biomass was evaluated by the equation:

$$SEC=\text{Absorbed power}/T,$$

wherein Absorbed power is measured in W, T is the material throughput, in Kg/h and SEC is measured in Wh/Kg.

The absorbed power is the electrical power absorbed by the electrical engine of the extruder. Thereby, the SEC parameter is an overestimation of the specific mechanical energy (SME), which is a parameter often reported in the prior art and is the mechanical energy applied to the thermally pretreated ligno-cellulosic biomass (see for example Wen-Hua Chen et al., Bioresource Technology 102 (2011), p. 10451).

The SEC was evaluated to be in the range of 0.1-0.2 kWh/Kg of thermally treated ligno-cellulosic biomass on wet basis. The specific energy consumption is much lower that the specific energy reported in the prior art, as for example in WO2011044292A2, wherein an energy of 1.03 kWh/kg is used.

The extruded thermally treated ligno-cellulosic biomass for reducing fiber shives is the exemplary thermally treated ligno-cellulosic biomass after fiber shives reduction used in the following examples and are indicated by the -ASR (After fiber Shives Reduction) extension following the sample code.

Composition

Composition of materials was determined according to standard analytical methods listed at the end of the experimental section to quantify soluble sugars (glucose, xylose, glucooligomers and xylooligomers), insoluble sugars (glucans and xylans), xylans degradation products (furans, such as furfural), glucans degradation products (HMF), and lignin and other compounds. The compositions of corresponding BSR and ASR materials were identical within the measurement error and only ASR compositions of exemplary samples (S01 to S06) are reported in Table 2. Results are reported in terms of weight percent of the dry matter of the samples. It is noted that the percent amount of glucans and xylans degradation products is negligible or very low, namely less than 1% in all the samples, thanks to the low severity of the thermal treatment. Acetic acid is produced as an effect of the thermal treatment on the acetyl groups in the ligno-cellulosic biomass and it is considered an enzyme inhibitory compound, but not a sugar degradation product which potentially limits the yield of the process. Also the content of acetic acid is negligible. It is noted that the percent ratio of insoluble xylans to insoluble glucans decreases with severity factor $R_{o2}$, as the thermal treatment removes preferentially xylans.

TABLE 2

Composition of thermally treated biomass after fiber shives reduction.

| Composition, % wt. DB | S1-ASR | S2-ASR | S3-ASR | S4-ASR | S5-ASR | S6-ASR |
|---|---|---|---|---|---|---|
| Glucose | 0 | 0 | 0 | 0 | 0.101 | 0.088 |
| Xylose | 0 | 0.244 | 0 | 0.8 | 1.734 | 1.546 |

TABLE 2-continued

Composition of thermally treated biomass after fiber shives reduction.

| Composition, % wt. DB | S1-ASR | S2-ASR | S3-ASR | S4-ASR | S5-ASR | S6-ASR |
|---|---|---|---|---|---|---|
| Glucolygomers | 0 | 0.258 | 0 | 0.556 | 0.77 | 0.731 |
| Xylolygomers | 0 | 3.849 | 0 | 4.886 | 2.112 | 2.634 |
| Insoluble glucans | 43.658 | 46.392 | 50.271 | 47.844 | 42.705 | 44.394 |
| Insoluble xylans | 13.498 | 14.637 | 13.046 | 11.122 | 3.994 | 3.79 |
| Lignin | 20.685 | 22.498 | 23.225 | 22.61 | 21.34 | 22.723 |
| Others | 22.159 | 11.933 | 13.458 | 11.945 | 26.656 | 23.351 |
| Furfural | 0 | 0.007 | 0 | 0.024 | 0.057 | 0.08 |
| HMF | 0 | 0.024 | 0 | 0.043 | 0.119 | 0.142 |
| Acetic Acid | 0 | 0.158 | 0 | 0.17 | 0.412 | 0.521 |
| Insoluble xylans/insoluble glucans | 0.309 | 0.316 | 0.26 | 0.232 | 0.094 | 0.085 |
| Insoluble glucans/lignin | 2.11 | 2.06 | 2.16 | 2.12 | 2.00 | 1.95 |

Glucose/Xylose Recovery and Glucans Accessibility

Glucose recovery is the percent ratio between the total amount of glucans in the thermally treated biomass before fiber shives reduction (as glucose equivalent calculated including insoluble glucans, gluco-oligomers, cellobiose and glucose present in both solid and liquid streams) and the amount of glucans (converted in glucose equivalent) present in the raw material before the thermally treatment. The complementary to 100% of the glucose recovery represent therefore the total amount of glucans degradation products as an effect of the thermal treatment.

Xylose recovery is the percent ratio between the total amount of xylans in the thermally treated biomass before fiber shives reduction (as xylose equivalent calculated including insoluble xylans, xylo-oligomers, xilobiose and xylose present in both solid and liquid streams) and the amount of xylans (converted in xylose equivalent) present in the raw material before the thermal treatment. The complementary to 100% of the xylose recovery represents therefore the total amount of xylans degradation products as an effect of the thermal treatment.

Glucans accessibility is defined as the percent amount of insoluble glucans enzymatically hydrolyzed to soluble compounds with respect to the amount of insoluble glucans in the pre-treated materials (before and after fiber shives reduction) and calculated as (1−% insoluble glucans at the end of the hydrolysis)/(% insoluble glucans at the beginning of the hydrolysis), when hydrolysis is conducted in excess of enzymes and for a long time. Glucans accessibility was determined according to the following procedure.

Pretreated material was mixed with water in a volume of 1500 ml to obtain a mixture having a 7.5% dry matter content and the mixture was inserted into an enzymatic reactor. pH was set to 5.2 and temperature was set to 50° C. An enzyme cocktail (CTec3 by Novozymes) was added, corresponding to a concentration of 26 g of cocktail solution per 100 gram of glucans contained in the mixture.

Enzymatic hydrolysis was carried out for 48 hours under agitation. The content of glucans, glucose and glucooligomers in the mixture was measured at different times of the enzymatic hydrolysis.

Glucans accessibility and xylose and glucose recovery was determined for all the BSR and ASR materials.

In FIG. 2 the glucans accessibility and in FIG. 3 the xylose and glucose recovery in function of $R_{02}$ are reported.

All the plots in this experimental section are reported in function of $R_{02}$, as this severity factor is related to the steam explosion effect. Similar considerations hold in the case that $R_0$ is considered as the independent variable in the graphs.

It is noted that glucans accessibility of BSR material increases by increasing severity factor, but a bigger amount of xylans are degraded. The fiber shives reduction treatment is effective to increase the glucans accessibility at low severity factor, without degrading xylans (or degrading a very few amount of) to degradation products. Thereby, also at low severity factor, a glucans accessibility greater than 90% is obtained. Increasing the severity factor, the effectiveness of the fiber shives reduction treatment on glucans accessibility is less pronounced.

In the case of glucans recovery, the degradation effect is less pronounced but the effects of thermal and fiber shives reduction treatment are similar to those observed for xylans recovery.

Automated Optical Analyses

The samples were analyzed by automated optical analysis, using unpolarized light for determining fibres, fines and fiber shives content, as well as length and width. ISO 16065 2:2007 protocol was used in fibres analyses.

The instrument used was a MorFi analyser from Techpap, Grenoble, France.

Briefly, 2 g of air dried sample was disintegrated in a low consistency pulper for 2000 revolutions in approximately 2 litres of tap water, thus reaching a stock concentration of about 1 g/l.

The suspension was stirred very well before withdrawing the sample to perform the measurement according to the manufacturer's instructions. Each sample was run in duplicate or in triplicate in case of higher standard deviation.

According to Morfi analysis software, the treated lignocellulosic biomass is composed by:

Fiber shives: elements having a width greater than 75 micron

Fibres: elements having a width equal to or less than 75 micron and a length greater than 200 micron Fines: having a width equal to or less than 75 micron and a length less than 200 micron The width of the fibres, fines and fibers shives remained substantially unchanged after the fiber shives reduction treatment.

In the graphs of FIG. 4 it is reported the area-weighted distribution of fibres and fines length of BSR and ASR materials produced at low severity factor (S02-BSR and S02-ASR, FIG. 4a) and high severity factor (S05-BSR and S05-ASR, FIG. 4b) relative to all the sample. Briefly, the percent area value of each length class has been calculated as percent ratio of the sum of the area of all the fibres and fines in each length class and the sum of the area of all the fines, fibres, and fiber shives.

It is noted that S05-BSR has a greater percent area of fines and a lower percent area of long fibres with respect to S02-BSR, as expected considering the higher severity of S05-BSR thermal treatment. This corresponds to a higher glucans accessibility of S05-BSR (about 95%) with respect to S02-BSR (84%).

The fiber shive reduction treatment reduces the percent area of long fibres (or equivalently the number of long fibres) and increases the population of fines and short fibres in both the samples, but:

the reduction of the percent area of long fibres in S05-ASR, with respect to S05-BSR, is similar to the corresponding reduction in S02-ASR;

the percent area of fines in S05-ASR is greater than in S02-ASR;

despite the fact that S05-ASR contains more fines/short fibres than S05-BSR (in other words, it is more refined), the accessibility is unchanged within the experimental error (93% and 94%);

despite the fact that S05-ASR contains more fines/short fibres than S02-ASR, the corresponding accessibility are very close (93% and 92% respectively).

In the graph of FIG. 5 it is reported the area-weighted distribution of fiber shives of S02-BSR (FIG. 5a) and S05-BSR (FIG. 5b) and related ASR materials. The percent area value of each length class has been calculated as percent ratio of the sum of the area of all the fiber shives in each length class to the sum of the areas of all the fines, fibres, and fiber shives.

It is highlighted that:

S05-BSR has a lower percent area of shives than S02-BSR, in particular shives longer than about 737 µm, evidencing that that steam explosion is effective in reducing big shives;

the percent area of shives is strongly reduced by the mechanical treatment in S02-BSR, due to the large starting shives population.

the accessibility of S02-BSR is strongly enhanced by the reduction in long shives population;

The accessibility of S05-BSR is not affected by the fiber shives reduction treatment because the limited percent area of long shives.

In the graph of FIG. 6 it is reported the percent area of all the shives having a length greater than 737 µm in function of the second severity cooking $R_{o2}$ of exemplary samples before and after fiber shives reduction. S06-BSR was produced at the maximum severity factor of $R_{o2}$ of 4.44 sufficient to remove substantially all shives. The percent area of all the shives having a length greater than 737 µm has been calculated as the percent ratio of the sum of the areas of all the shives and the sum of the areas of all the fines, fibres, and fiber shives.

These results highlight the fact that the increase in glucans accessibility is not strictly related to fibre size reduction, that is, once the fibres are accessible to the enzyme, any further decrease in fibre length is not effective on enzymatic accessibility of the fibre, thereby energy is spent without obtaining any beneficial effect on accessibility.

Instead, experiments show that it is the reduction of the amount of fiber shives to be effective on the enzymatic accessibility, depending clearly from the starting population of fiber shives. If the thermal treatment is performed at a severity high enough to produce a thermally treated material having a low amount of fiber shives, more specifically of long fiber shives, the fiber shives reduction treatment has not effect on the accessibility of the material. Unfortunately, such a high severity thermal treatment degrade a relevant amount of glucans and xylans to detrimental degradation products.

Basically, the experiments highlight that fiber shives are fiber bundles which are not accessible to the enzymes, thereby limiting the glucans accessibility, and that the fiber shives reduction treatment is useful when it convert fiber shives to fibres. As a consequence, the combination of the thermal treatment in mild conditions and the treatment to reduce the amount of fiber shives increases the glucans accessibility and xylose recovery without degrading a significant amount of sugars in the ligno-cellulosic biomass.

Torque Measurement of Slurried Samples

Torque measurement experiments were run in a cylindrical vessel whose characteristics are here reported.

D (diameter)=105 mm
H (height)=145 mm

The reactor is fitted with a stirrer tool IKA R 1375 to give the following configurations:

D (stirrer width)=70 mm
D (stirrer height)=70 mm
H (stirrer distance from the vessel bottom)=10 mm
Agitation was provided by IKA Eurostar 60 control motors (power: 126 W).

With no material inserted, the no load torque at 50 rpm was 0 N cm. An amount of material corresponding to 80 gr on dry basis was inserted in the vessel and water was added to reach a dry matter of 20%.

The mixture was agitated at 50 rpm for 10 seconds. The torque value of each run was calculated as the mean of the maximum and minimum value during 5 seconds measuring time.

The measurement was replicated three times and the torque was calculated as the mean value of the three runs.

After each torque measurement at a fixed dry matter, the dry matter was reduced to 18%, 16%, 14%, 12%, 10%, 8% by subsequent addition of water. Temperature was maintained to 25° C.

In table 3 torque values of exemplary samples, collected at different dry matter, are reported. Values below the sensitivity of the measurements are reported as 0.

TABLE 3

Torque measurements of samples at different dry matter
Torque, N * cm

| DM, % | S01-BSR | S01-ASR | S02-BSR | S02-ASR | S03-BSR | S03-ASR | S04-BSR | S04-ASR | S05-BSR | S05-ASR |
|---|---|---|---|---|---|---|---|---|---|---|
| 20% | 87 | 11 | 49 | 8 | 59 | 17 | 36 | 2 | 0 | 0 |
| 18% | 54 | 7 | 40 | 6 | 45 | 10 | 20 | 1 | 0 | 0 |
| 16% | 43 | 5 | 31 | 3 | 31 | 8 | 13 | 0 | 0 | 0 |
| 14% | 25 | 5 | 19 | 2 | 17 | 5 | 8 | 0 | 0 | 0 |
| 12% | 17 | 3 | 10 | 1 | 11 | 3 | 5 | 0 | 0 | 0 |
| 10% | 9 | 1 | 6 | 0 | 8 | 1 | 1 | 0 | 0 | 0 |
| 8% | 3 | 0 | 1 | 0 | 3 | 0 | 0 | 0 | 0 | 0 |

In FIG. 7 the torque of S01 and S04 samples (BSR and corresponding ASR materials), measured at different dry matter, are plotted as an example.

In FIG. 8 the torque measured at 18% dry matter as a function of the severity factor is reported.

It is noted that at fixed dry matter the torque values decreases by increasing the thermal treatment severity factor and that samples thermally treated at the highest severity factor present a torque value which is very small—or zero—even at the high dry matter values. Torque values are dependent from the experimental setup and procedure used, but they are directly related to viscosity measurements. Thereby, viscosity strongly decrease increasing the severity factor of the thermal treatment.

By applying the disclosed fiber shives reduction treatment to the thermally treated samples, the torque values at each dry matter decrease and this effect is enhanced at low severity.

Thereby, the combination of the thermal treatment in mild conditions and the treatment to reduce the amount of fibers shives of the thermally treated biomass strongly reduces the torque/viscosity of a slurry of the corresponding thermally treated biomass after fiber shives reduction. Again, this is obtained without degrading significant amount of sugars of the ligno-cellulosic biomass.

As reported in following experimental sections, the torque/viscosity values of the slurry prepared using the thermally treated ligno-cellulosic biomass after shives reduction are comparable to the torque/viscosity values of corresponding thermally treated biomass before fiber shives reduction which have been enzymatically hydrolyzed.

Saturation Humidity

Saturation humidity is the maximum amount of water that could be absorbed by the ligno-cellulosic biomass. The water added to the material after the material has reached its saturation humidity value is not entrapped into the solid material and will be present as free water outside the solid. Material properties evaluated using the saturation humidity procedure are equivalent to those given by the well-known in the art Water Retention Value (WRV) procedure. Saturation humidity procedure is easier and could be performed without dedicated equipment with respect to WRV.

Saturation humidity is correlated to torque/viscosity of the slurried ligno-cellulosic biomass, but it is related to not-slurried ligno-cellulosic biomass.

Saturation humidity was measured according to the following methodology:

An amount of 20 gr of sample on dry matter basis was inserted in a becker and water (up to 50 ml) was added in 2 ml aliquots every 1 h and hand shaken to allow the material adsorb the water. The procedure ends when water added is not absorbed into the material after the 1 h incubation and water drops are observed on the surface of the material. Measurements were performed at 25° C. The saturation humidity is calculated as the total amount of water absorbed into the material (initial moisture content plus the amount of water added), divided by the weight of the material on a dry basis.

The saturation humidity of samples prepared at different severity factor $R_{02}$ before and after fiber shives reduction is reported in FIG. 9. One of the effects of the disclosed fiber shives reduction treatment is to reduce the saturation humidity, and this result is also correlated to the decrease of torque/viscosity observed for ASR slurries with respect to BSR slurry. It is noted that in the prior art an increase of WRV (which is equivalent to saturation humidity) is usually related to micro-fibrillation of fibres, that is a mechanical treatment used to open up the fibres that consequently adsorb more water (see I. C. Hoeger et al., Cellulose (2013)20:807-818).

A similar concept is expressed in S. H. Lee et al., Bioresource Technology, 2010, 101, p. 9645-9649, and in S. H. Lee et al., Bioresource Technology, 2010, 101, p. 769-774, where a thermally treated biomass is subjected to a mechanical treatment by means on an extruder operated in condition to fibrillate the feedstock into submicron and/or nanoscale fibres, even if no WRV/saturation humidity measurements are presented.

Thereby, according to the prior art consideration, the fiber shives reduction treatment presently disclosed does not fibrillate the fibres.

Comparison of Torque of Slurried Thermally Treated Biomass after Fiber Shives Reduction and Thermally Treated Biomass Before Fiber Shives Reduction During Enzymatic Hydrolysis To better demonstrate the importance of forming a low viscosity slurry from the thermally treated biomass after shives reduction without any added enzymes, a further sample was prepared, at the following conditions:

| Ligno-cellulosic biomass | Soaking | | Steam explosion | | | | |
| --- | --- | --- | --- | --- | --- | --- | --- |
| | Temperature (° C.) | Time (minutes) | Temperature (° C.) | Time (minutes) | $R_{01}$ | $R_{02}$ | $R_0$ |
| Wheat straw | 155 | 65 | 190 | 4 | 3.43 | 3.25 | 3.65 |

Fiber shives reduction step was performed by means of the extruder according to the process previously described.

Torque measurement experiments were run in two identical anchor impeller, herein referred to reactor A and reactor B, whose characteristics are here reported.

T (reactor diameter)=0.15 m–Z (reactor height)=0.30 m
jacket for heat exchange fluid all around the lateral surface and bottom, with a width of 4 cm;
hemi-spherical bottom;
cover with gasket and seal, with 5 openings (1 center hole for stirrer shaft; 4 side holes to add materials or for sampling, that during the tests will be closed with caps).

The two reactors are fitted with two identical anchor agitators to give the following configurations:
D ("wingspan")=0.136 m
S (blade width)=0.019 m
H (anchor height)=0.146 m
5 C (clearance, blade-wall distance)=0.007 m
Agitation was provided by Heidolph RZR 2102 control motors (power: 140 W).

With no material inserted, the no load torque at 23 rpm was 23 N cm. An amount of 800 gr of BSR material having a moisture content of 60% was inserted in reactor A and soaking liquid was added at a ratio of 1:0.67. The dry matter was progressively adjusted to reach a final dry matter of 15% by addition of water at the end of the experiment.

An amount of 800 gr of ASR material having a dry matter content of 40% was inserted in reactor B and soaking liquid was added at a ratio of 1:0.67. The dry matter was progressively adjusted to reach a final dry matter of 15% by addition of water at the end of the experiment.

Temperature in both reactors was 25° C.

The two mixtures were agitated at 23 rpm for 90 minutes with no enzymes added.

Viscosity reduction was then conducted in both reactors, at a temperature of 50° C. pH was corrected to 5 by means of a KOH solution. Viscosity reduction was conducted by inserting Ctec3 enzymatic cocktail by Novozymes at a concentration of 4.5 gr of enzyme cocktail every 100 g gram of glucans contained in the BSR and ASR solid materials. Viscosity reduction was conducted for 48 hours under agitation.

Torque was recorded for all the experiment time. No load torque was subtracted by the measured torque. The torque of the mixture comprising the material before fiber shives reduction without enzymes was approximately constant at a value close to 110 N cm till the insertion of enzymes. Then torque value was found to decrease after enzyme addition as usually occurs during hydrolysis. The torque of the mixture comprising the material after fiber shives reduction was found to be very low and close to the torque value of the hydrolyzed stream even before enzymes addition.

FIG. 10 reports torque values of the two slurries during the first 21 hours of mixing time. Torque values remained approximately constant after this period and for the remaining mixing time in both reactors. Time zero corresponds to the start of agitation. Arrows indicate enzymes addition in both reactors.

Rheological and Viscosity measurements

Different amounts of BSR and ASR of the sample having $R_{02}=3.25$ were added to water to prepare 600 ml slurry samples at different dry matter content on dry basis, ranging from 5 to 17%. The samples were agitated up to 15 minutes until reaching a visually well dispersed slurries.

Rheological measurements were performed using a RheolabQC at 25° C. Data were collected corresponding to a shear rate ranging from 0.01 to 100 s$^{-1}$ and at a slope of 6 Pt./dec. Table 4 reports the measured shear stress and viscosity values for ASR slurries having a dry matter of 5%, 7%, 9%, 11%. The viscosity is not constant and decreases with the increase of shear rate.

It was not possible to measure BSR slurries on RheolabQC at 25° C. even at a dry matter lower than 5% due to the high viscosity of the sample. This is a remarkable difference in the rheological properties of BSR and ASR slurries.

TABLE 4

Rheological parameters of ASR slurries having a dry matter content of 5%, 7%, 9%, 11%.

| Shear Rate, | Shear Stress, Pa | | | | Viscosity, Pa · s | | | |
|---|---|---|---|---|---|---|---|---|
| | Dry matter | | | | | | | |
| 1/s | 5% | 7% | 9% | 11% | 5% | 7% | 9% | 11% |
| 0.10 | 0.72 | 0.69 | 1.11 | 18.10 | 7.2 | 6.90 | 11.1 | 181 |
| 0.15 | 0.68 | 0.82 | 0.71 | 20.30 | 4.66 | 5.60 | 4.84 | 138 |
| 0.22 | 0.63 | 1.26 | 0.62 | 23.60 | 2.9 | 5.87 | 2.9 | 110 |
| 0.32 | 0.62 | 1.84 | 0.94 | 27.70 | 1.97 | 5.82 | 2.97 | 87.7 |
| 0.46 | 1.14 | 1.63 | 1.33 | 35.10 | 2.47 | 3.50 | 2.87 | 75.7 |
| 0.68 | 0.96 | 1.53 | 0.64 | 47.70 | 1.41 | 2.25 | 0.932 | 70.1 |
| 1.00 | 1.17 | 1.16 | 1.19 | 58.10 | 1.17 | 1.16 | 1.19 | 58.2 |
| 1.47 | 0.81 | 0.67 | 1.01 | 43.20 | 0.553 | 0.45 | 0.687 | 29.3 |
| 2.15 | 0.67 | 1.00 | 1.35 | 10.70 | 0.31 | 0.47 | 0.627 | 4.94 |
| 3.16 | 1.36 | 1.77 | 1.00 | 27.10 | 0.429 | 0.56 | 0.317 | 8.61 |
| 4.64 | 0.54 | 1.11 | 1.78 | 18.50 | 0.117 | 0.24 | 0.383 | 3.97 |
| 6.81 | 0.77 | 1.33 | 1.96 | 36.60 | 0.113 | 0.20 | 0.288 | 5.36 |
| 10.00 | 0.74 | 1.56 | 3.23 | 25.30 | 0.074 | 0.16 | 0.323 | 2.53 |
| 14.70 | 1.09 | 1.64 | 4.35 | 28.20 | 0.074 | 0.11 | 0.296 | 1.92 |
| 21.50 | 1.16 | 1.89 | 5.61 | 26.20 | 0.053 | 0.09 | 0.26 | 1.21 |
| 31.60 | 1.61 | 2.05 | 5.05 | 22.40 | 0.050 | 0.06 | 0.16 | 0.70 |
| 46.40 | 0.73 | 2.75 | 4.63 | 24.90 | 0.015 | 0.06 | 0.099 | 0.53 |
| 68.10 | 0.37 | 2.45 | 5.84 | 24.30 | 0.005 | 0.04 | 0.085 | 0.35 |
| 100.00 | 0.44 | 2.62 | 4.36 | 21.60 | 0.004 | 0.03 | 0.043 | 0.21 |

Figure 11:
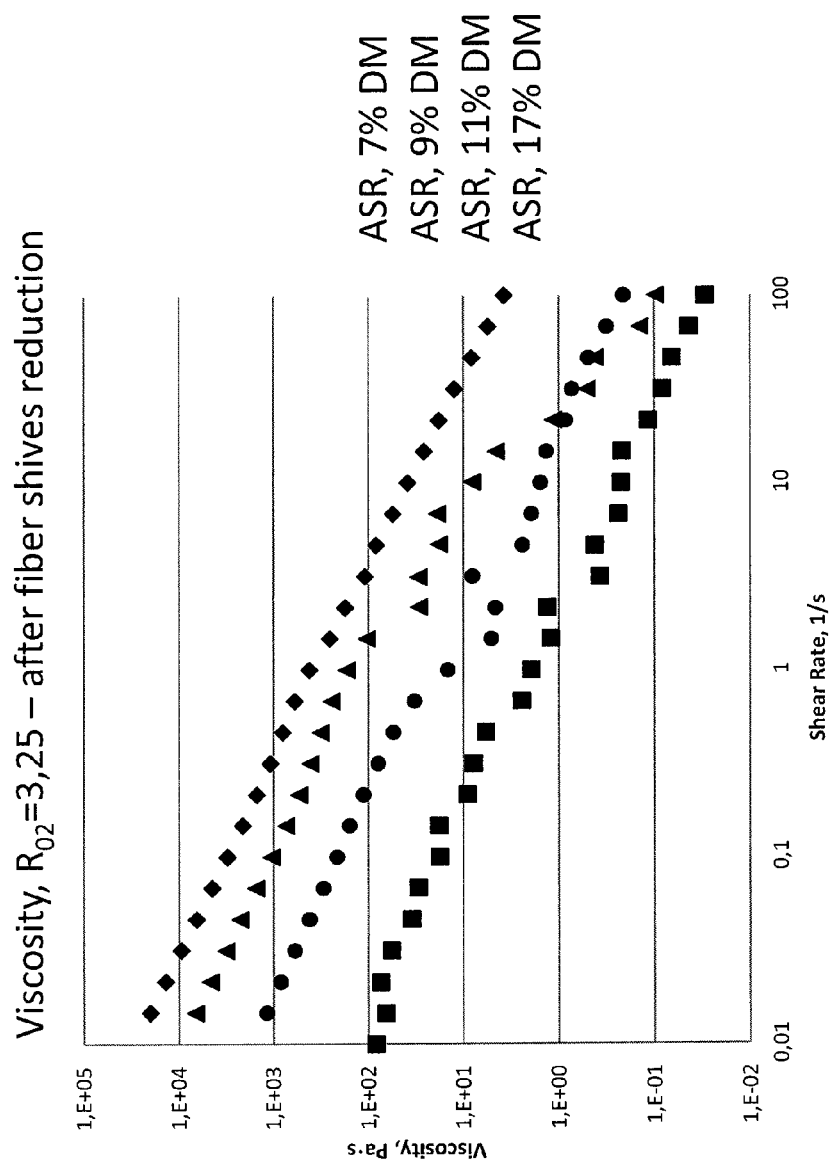
FIG. 11 plots the viscosity of slurries of the thermally treated biomass after fiber shives reduction at different amounts in water.

The viscosity of ASR slurries at 7%, 9%, 11% and 17% are reported in the graph of FIG. 11 on a bi-logarithmic scale. The vertical line in the graph indicates the shear rate value which was selected as the reference value for measuring the viscosity. In the context of the present disclosure, the described RheolabQC instrument procedure for viscosity measurement is the reference method for measuring the viscosity of a slurry.

Figure 12:
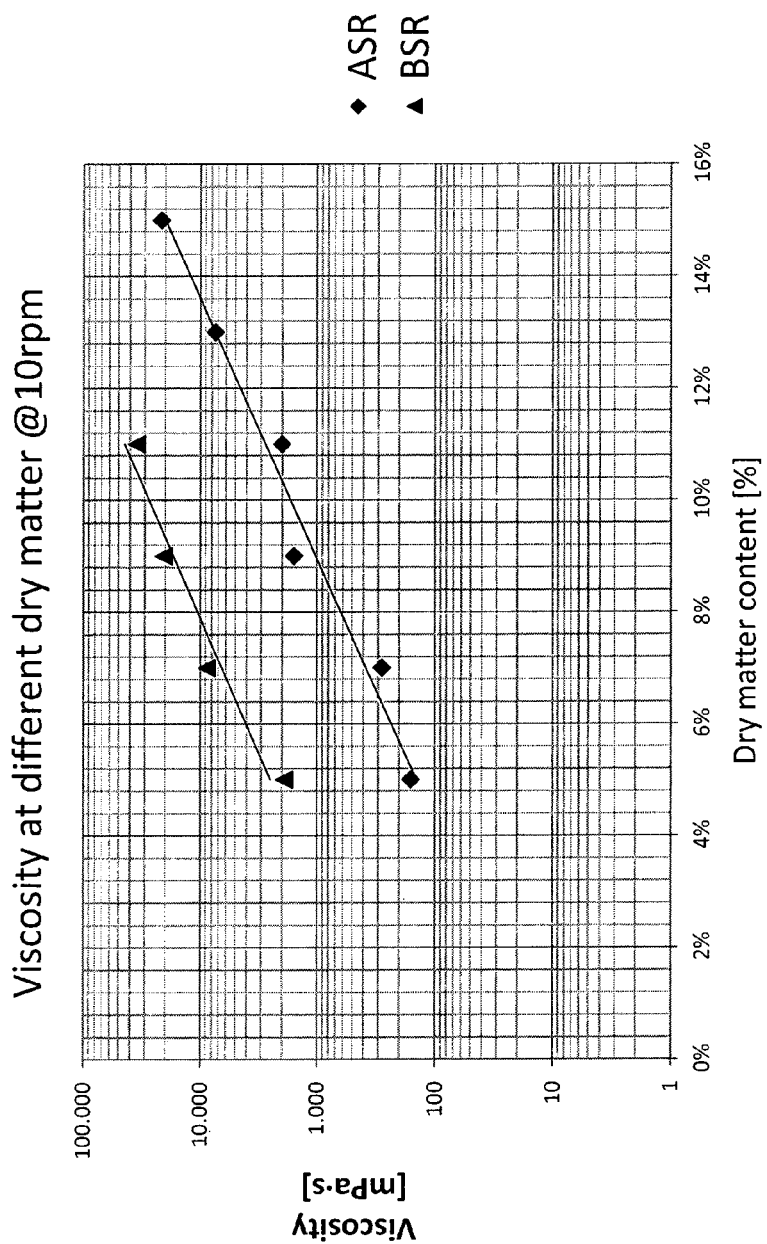
FIG. 12 plots the viscosity of slurries of thermally treated ligno-cellulosic biomass before and after fiber shives reduction at different dry matter contents of the slurry.

Viscosity measurements were performed on BSR and ASR slurry samples also using a Brookfield RVDV-I Prime viscometer following the procedures reported by the producer. All the measurements were performed at 25° C. using a disc spindle #5 on a 600 ml sample. Data were collected starting from 1 rpm and increasing the rotation speed to 2.5, 5, 10, 20, 50 and 100 rpm. In FIG. 12 viscosities of BSR and ASR slurries collected at 10 rpm as a function of dry matter are shown. The graph highlights that the viscosity of the slurry prepared using ASR is about 90% less than that prepared using BSR.

Analytical Methods

Analytical measurements were performed according to the following NREL standards Determination of Structural Carbohydrates and Lignin in Biomass Laboratory Analytical Procedure (LAP) Issue Date: Apr. 25, 2008

*Technical Report* NREL/TP-510-42618 Revised April 2008

Determination of Extractives in Biomass

Laboratory Analytical Procedure (LAP) Issue Date: Jul. 17, 2005

*Technical Report* NREL/TP-510-42619 January 2008

Preparation of Samples for Compositional Analysis

Laboratory Analytical Procedure (LAP) Issue Date: Sep. 28, 2005

*Technical Report* NREL/TP-510-42620 January 2008

Determination of Total Solids in Biomass and Total Dissolved Solids in Liquid Process Samples Laboratory Analytical Procedure (LAP) Issue Date: Mar. 31, 2008

*Technical Report* NREL/TP-510-42621 Revised March 2008

Determination of Ash in Biomass

Laboratory Analytical Procedure (LAP) Issue Date: Jul. 17, 2005

*Technical Report* NREL/TP-510-42622 January 2008

Determination of Sugars, by Products, and Degradation Products in Liquid Fraction Process Samples Laboratory Analytical Procedure (LAP) Issue Date: Dec. 8, 2006

*Technical Report* NREL/TP-510-42623 January 2008

Determination of Insoluble Solids in Pretreated Biomass Material

Laboratory Analytical Procedure (LAP) Issue Date: Mar. 21, 2008

NREL/TP-510-42627 March 2008

The invention claimed is:

1. A process for converting a thermally treated ligno-cellulosic biomass comprising cellulose and lignin derived from a ligno-cellulosic feedstock into at least one polyol, said thermally treated ligno-cellulosic biomass being in physical forms of at least fibres, fines and fiber shives, wherein:
  i. the fibres each have a width of 75 μm or less, and a fibre length greater than or equal to 200 μm,
  ii. the fines each have a width of 75 μm or less, and a fine length less than 200 μm,
  iii. the fiber shives each have a width greater than 75 μm with a first portion of the fiber shives each having a shive length less than 737 μm and a second portion of the fiber shives each having a shive length greater than or equal to 737 μm;

wherein the process comprises the steps of:
  a. reducing the fiber shives of the thermally treated ligno-cellulosic biomass, wherein the percent area of fiber shives having a shive length greater than or equal to 737 μm relative to the total area of fiber shives, fibres and fines of the thermally treated ligno-cellulosic biomass after fiber shives reduction is less than the percent area of fiber shives having a shive length greater than or equal to 737 μm relative to the total area of fiber shives, fibres and fines of the thermally treated ligno-cellulosic biomass before fiber shives reduction, wherein the percent area is measured by automated optical analysis;
b. dispersing an amount of the thermally treated ligno-cellulosic biomass before, during or after fiber shives reduction into an amount of a carrier liquid to create a slurry stream;
c. contacting in a reaction zone, hydrogen, water, and the slurry stream, with a catalyst system at reaction conditions to generate an effluent stream comprising the at least one polyol;
d. separating hydrogen from the effluent stream and recycling at least a portion of the separated hydrogen to the reaction zone;
e. separating water from the effluent stream and recycling at least a portion of the separated water to the reaction zone; and
f. recovering the at least one polyol from the effluent stream.

2. The process according to claim 1, wherein a part of the fiber shives reduction is done by separating at least a portion of the fiber shives having a shive length greater than or equal to 737 μm from the thermally treated ligno-cellulosic biomass.

3. The process of claim 1, wherein a part of the fiber shives reduction is done by converting at least a portion of the fiber shives having a shive length greater than or equal to 737 μm in the thermally treated ligno-cellulosic biomass to fibres or fines.

4. The process of claim 1, wherein at least a part of the fiber shives reduction step is done by applying a work in a form of mechanical forces to the thermally treated ligno-cellulosic biomass, and all the work done by all the forms of mechanical forces on the thermally treated ligno-cellulosic biomass is less than 500 Wh/KG per kg of the thermally treated ligno-cellulosic biomass on a dry basis.

5. The process of claim 4, wherein the mechanical energy applied to the thermally treated ligno-cellulosic biomass is not mechanical energy derived from free-fall or gravity mixing.

6. The process of claim 5, wherein the mechanical forces are applied using a machine selected from the group consisting of single screw extruders, twin screw extruders, and banburies.

7. The process of claim 1, wherein the slurry stream has a viscosity less than a value selected from the group consisting of 0.1 Pa s, 0.3 Pa s, 0.5 Pa s, 0.7 Pa s, 0.9 Pa s, 1.0 Pa s, 1.5 Pa s, 2.0 Pa s, 2.5 Pa s, 3.0 Pa s, 4 Pa s, 5 Pa s, 7 Pa s, 9 Pa s, and 10 Pa s, wherein the viscosity is measured at 25° C., at a shear rate of $10\ s^{-1}$ and at a dry matter content of 7% by weight of the slurry stream.

8. The process of claim 7, wherein the dry matter content of the slurry stream by weight is greater than a value selected from the group consisting of 5%, 7%, 8%, 10%, 12%, 15%, 18%, 20%, 25%, 30%, 35%, and 40%.

9. The process of claim 1, wherein the percent area of the fiber shives having a shive length greater than or equal to 737 μm relative to the total area of fiber shives, fibres and fines of the thermally treated ligno-cellulosic biomass after fiber shives reduction is less than a value selected from the group consisting of 1%, 0.5%, 0.25%, 0.2% and 0.1%.

10. The process of claim 1, wherein the slurry stream does not contain ionic groups derived from added mineral acids, mineral bases, organic acids, or organic bases.

11. The process of claim 1, wherein the thermally treated ligno-cellulosic biomass has been steam exploded before fiber shives reduction.

12. The process of claim 1, further comprises the step of adding a hydrolysis catalyst to the slurry to hydrolyze at least a portion of the cellulose to glucose.

13. The process of claim 1, wherein the catalyst system comprises an unsupported component comprising a compound selected from the group consisting of a tungsten compound, a molybdenum compound, and any combination thereof, and a supported compound comprising a supported active metal component selected from the group consisting of Pt, Pd, Ru, Rh, Ni, Ir, and combinations thereof on a solid catalyst support.

14. The process of claim 1, wherein the catalyst system comprises a metal component selected from the group consisting of IUPAC Groups 4, 5 and 6 of the Periodic Table, the metal component having an oxidation state greater than or equal to 2+ wherein the metal component is in a form other than a carbide, nitride or phosphide, and a hydrogenation component selected from the group consisting of IUPAC Groups 8, 9, and 10, of the Periodic Table.

15. The process of claim 13, wherein the slurry stream comprises at least a carbohydrate and wherein the conversion of the at least a carbohydrate in the slurry stream to the at least one polyol is operated in a mode selected from the group consisting of batch mode operation and continuous mode operation.

16. The process of claim 1, further comprising separating at least one co-product from the effluent stream and recycling at least a portion of the separated co-product to the reaction zone.

17. The process of claim 1, wherein the effluent stream further comprises cellulose and the process further comprises separating the cellulose from the effluent stream and recycling at least a portion of the separated cellulose to the reaction zone.

18. The process of claim 1, wherein the effluent stream further comprises at least a portion of the catalyst system, said process further comprising separating at least a portion of the catalyst from the effluent stream and recycling separated catalyst to the reaction zone.

19. The process of claim 18, further comprising reactivating the separated catalyst prior to recycling the catalyst to the reaction zone; wherein the catalyst system is separated from the effluent stream using a technique selected from the group consisting of direct filtration, settling followed by filtration, hydrocyclone, fractionation, centrifugation, the use of flocculants, precipitation, liquid extraction, evaporation, and combinations thereof; and at least a portion of the catalyst system is separated from the effluent stream after the hydrogen is separated from the effluent stream, and before the water is separated from the effluent stream.

20. The process of claim 1, wherein the reaction zone comprises a mixing zone upstream of a reactor and wherein the separated hydrogen is recycled to the reactor and the separated water is recycled to the mixing zone.

21. The process of claim 16, wherein the reaction zone comprises a mixing zone upstream of a reactor and wherein at least a portion of the separated at least one co-product is recycled to the reactor, the mixing zone, or both.

22. The process of claim 1, wherein the hydrogen is separated from the effluent stream before the water is separated from the effluent stream.

23. The process of claim 16, wherein the at least one co-product is separated after the hydrogen and the water are separated from the effluent stream.

24. The process of claim 16, wherein the at least one co-product is selected from the group consisting of alcohols, organic acids, aldehydes, monosaccharides, polysaccharides, phenolic compounds, hydrocarbons, glycerol, depolymerized lignin, carbohydrates, and proteins.

25. The process of claim 1, wherein the reaction zone comprises at least a first input stream and a second input stream, the first input stream comprising at least the feedstock comprising cellulose and the second input stream comprising hydrogen.

26. The process of claim 25, wherein the first input stream is pressurized prior to the reaction zone and the second input stream is pressurized and heated prior to the reaction zone.

27. The process of claim 25, wherein the first input stream is pressurized and heated to a temperature below the decomposition temperature of the cellulose prior to the reaction zone and the second input stream is pressurized and heated prior to the reaction zone.

28. The process of claim 25, wherein the first input stream and the second input stream further comprise water.

29. The process of claim 1, wherein the reaction zone comprises a system selected from the group consisting of an ebullating catalyst bed reaction system, an immobilized catalyst reaction system having catalyst channels, an augured reaction system, a fluidized bed reaction system, a mechanically mixed reaction system, and a slurry reactor system.

30. The process of claim 1, wherein the at least one polyol comprises a compound selected from the group consisting of ethylene glycol, propylene glycol and mixture thereof.

* * * * *